(12) United States Patent
Shishkov et al.

(10) Patent No.: US 8,145,018 B2
(45) Date of Patent: Mar. 27, 2012

(54) APPARATUS FOR OBTAINING INFORMATION FOR A STRUCTURE USING SPECTRALLY-ENCODED ENDOSCOPY TECHNIQUES AND METHODS FOR PRODUCING ONE OR MORE OPTICAL ARRANGEMENTS

(75) Inventors: Milen Shishkov, Watertown, MA (US); Guillermo J. Tearney, Cambridge, MA (US); Brett Eugene Bouma, Quincy, MA (US); Dvir Yelin, Brookline, MA (US); Nicusor Iftimia, North Chelmsford, MA (US)

(73) Assignee: The General Hospital Corporation, Boston, MA (US)

( * ) Notice: Subject to any disclaimer, the term of this patent is extended or adjusted under 35 U.S.C. 154(b) by 1347 days.

(21) Appl. No.: 11/623,852

(22) Filed: Jan. 17, 2007

(65) Prior Publication Data

US 2007/0188855 A1    Aug. 16, 2007

Related U.S. Application Data

(60) Provisional application No. 60/760,139, filed on Jan. 19, 2006.

(51) Int. Cl.
G02B 6/32 (2006.01)
G02B 6/34 (2006.01)
G02B 6/06 (2006.01)

(52) U.S. Cl. .......... 385/33; 385/31; 385/34; 385/36; 385/37; 385/38; 385/39; 385/49; 385/115; 385/116; 385/117; 385/119

(58) Field of Classification Search .......... 385/31, 385/33, 34, 37, 39, 117, 118, 119
See application file for complete search history.

(56) References Cited

U.S. PATENT DOCUMENTS

| | | | |
|---|---|---|---|
| 3,090,753 A | 5/1963 | Matuszak et al. | |
| 3,601,480 A | 8/1971 | Randall | |
| 3,856,000 A | 12/1974 | Chikama | |
| 3,872,407 A | 3/1975 | Hughes | |

(Continued)

FOREIGN PATENT DOCUMENTS

DE    4105221    9/1991

(Continued)

OTHER PUBLICATIONS

Liptak David C. et al., (2007) "On the Development of a Confocal Rayleight-Brillouin Microscope" *American Institute of Physics* vol. 78, 016106.

(Continued)

*Primary Examiner* — Ryan Lepisto
(74) *Attorney, Agent, or Firm* — Dorsey & Whitney LLP

(57) ABSTRACT

Exemplary apparatus for obtaining information for a structure can be provided. For example, first optical fiber arrangement(s) can be provided which transceives at least one first electro-magnetic radiation, and can include at least one fiber. Second focusing arrangement(s) can be provided in optical communication with the optical fiber arrangement. The second arrangement can be configured to focus and provide there through the first electro-magnetic radiation. Third dispersive arrangement(s) can receive a particular radiation which is the first electro-magnetic radiation and/or the focused electro-magnetic radiation, and forward a dispersed radiation thereof to at least one section of the structure. At least one end of the fiber can be directly connected to the second focusing arrangement and/or the third dispersive arrangement.

16 Claims, 11 Drawing Sheets

U.S. PATENT DOCUMENTS

| | | | |
|---|---|---|---|
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,030,831 A | 6/1977 | Gowrinathan | |
| 4,140,364 A | 2/1979 | Yamashita et al. | |
| 4,141,362 A | 2/1979 | Wurster | |
| 4,224,929 A | 9/1980 | Furihata | |
| 4,295,738 A | 10/1981 | Meltz et al. | |
| 4,300,816 A | 11/1981 | Snitzer et al. | |
| 4,303,300 A | 12/1981 | Pressiat et al. | |
| 4,428,643 A | 1/1984 | Kay | |
| 4,479,499 A | 10/1984 | Alfano | |
| 4,533,247 A | 8/1985 | Epworth | |
| 4,585,349 A | 4/1986 | Gross et al. | |
| 4,601,036 A | 7/1986 | Faxvog et al. | |
| 4,607,622 A | 8/1986 | Fritch et al. | |
| 4,631,498 A | 12/1986 | Cutler | |
| 4,639,999 A * | 2/1987 | Daniele | 438/34 |
| 4,650,327 A | 3/1987 | Ogi | |
| 4,744,656 A | 5/1988 | Moran et al. | |
| 4,751,706 A | 6/1988 | Rohde et al. | |
| 4,763,977 A | 8/1988 | Kawasaki et al. | |
| 4,770,492 A | 9/1988 | Levin et al. | |
| 4,827,907 A | 5/1989 | Tashiro et al. | |
| 4,834,111 A | 5/1989 | Khanna et al. | |
| 4,868,834 A | 9/1989 | Fox et al. | |
| 4,890,901 A | 1/1990 | Cross, Jr. | |
| 4,892,406 A | 1/1990 | Waters | |
| 4,905,169 A | 2/1990 | Buican et al. | |
| 4,909,631 A | 3/1990 | Tan et al. | |
| 4,925,302 A | 5/1990 | Cutler | |
| 4,928,005 A | 5/1990 | Lefèvre et al. | |
| 4,965,441 A | 10/1990 | Picard | |
| 4,965,599 A | 10/1990 | Roddy et al. | |
| 4,984,888 A | 1/1991 | Tobias et al. | |
| 4,993,834 A | 2/1991 | Carlhoff et al. | |
| 4,998,972 A | 3/1991 | Chin et al. | |
| 5,039,193 A | 8/1991 | Snow et al. | |
| 5,040,889 A | 8/1991 | Keane | |
| 5,045,936 A | 9/1991 | Lobb et al. | |
| 5,046,501 A | 9/1991 | Crilly | |
| 5,065,331 A | 11/1991 | Vachon et al. | |
| 5,085,496 A | 2/1992 | Yoshida et al. | |
| 5,120,953 A | 6/1992 | Harris | |
| 5,121,983 A | 6/1992 | Lee | |
| 5,127,730 A | 7/1992 | Brelje et al. | |
| 5,197,470 A | 3/1993 | Helfer et al. | |
| 5,202,745 A | 4/1993 | Sorin et al. | |
| 5,202,931 A | 4/1993 | Bacus et al. | |
| 5,208,651 A | 5/1993 | Buican | |
| 5,212,667 A | 5/1993 | Tomlinson et al. | |
| 5,214,538 A | 5/1993 | Lobb | |
| 5,228,001 A | 7/1993 | Birge et al. | |
| 5,241,364 A | 8/1993 | Kimura et al. | |
| 5,248,876 A | 9/1993 | Kerstens et al. | |
| 5,250,186 A | 10/1993 | Dollinger et al. | |
| 5,262,644 A | 11/1993 | Maguire | |
| 2,339,754 A | 1/1994 | Brace | |
| 5,275,594 A | 1/1994 | Baker | |
| 5,281,811 A * | 1/1994 | Lewis | 250/226 |
| 5,291,885 A | 3/1994 | Taniji et al. | |
| 5,293,872 A | 3/1994 | Alfano et al. | |
| 5,293,873 A | 3/1994 | Fang | |
| 5,304,173 A | 4/1994 | Kittrell et al. | |
| 5,304,810 A | 4/1994 | Amos | |
| 5,305,759 A | 4/1994 | Kaneko et al. | |
| 5,317,389 A | 5/1994 | Hochberg et al. | |
| 5,318,024 A | 6/1994 | Kittrell et al. | |
| 5,321,501 A | 6/1994 | Swanson et al. | |
| 5,348,003 A | 9/1994 | Caro | |
| 5,353,790 A | 10/1994 | Jacques et al. | |
| 5,383,467 A | 1/1995 | Auer et al. | |
| 5,394,235 A | 2/1995 | Takeuchi et al. | |
| 5,404,415 A | 4/1995 | Mori et al. | |
| 5,411,016 A | 5/1995 | Kume et al. | |
| 5,419,323 A | 5/1995 | Kittrell et al. | |
| 5,424,827 A | 6/1995 | Horwitz et al. | |
| 5,439,000 A | 8/1995 | Gunderson et al. | |
| 5,441,053 A | 8/1995 | Lodder et al. | |
| 5,450,203 A | 9/1995 | Penkethman | |
| 5,454,807 A | 10/1995 | Lennox et al. | |
| 5,459,325 A | 10/1995 | Hueton et al. | |
| 5,459,570 A | 10/1995 | Swanson et al. | |
| 5,465,147 A | 11/1995 | Swanson | |
| 5,486,701 A | 1/1996 | Norton et al. | |
| 5,491,524 A | 2/1996 | Hellmuth et al. | |
| 5,491,552 A | 2/1996 | Knuttel | |
| 5,526,338 A | 6/1996 | Hasman et al. | |
| 5,555,087 A | 9/1996 | Miyagawa et al. | |
| 5,562,100 A | 10/1996 | Kittrell et al. | |
| 5,565,983 A | 10/1996 | Barnard et al. | |
| 5,565,986 A | 10/1996 | Knuttel | |
| 5,566,267 A | 10/1996 | Neuberger | |
| 5,583,342 A | 12/1996 | Ichie | |
| 5,590,660 A | 1/1997 | MacAulay et al. | |
| 5,600,486 A | 2/1997 | Gal et al. | |
| 5,601,087 A | 2/1997 | Gunderson et al. | |
| 5,621,830 A | 4/1997 | Lucey et al. | |
| 5,623,336 A | 4/1997 | Raab et al. | |
| 5,635,830 A | 6/1997 | Itoh | |
| 5,649,924 A | 7/1997 | Everett et al. | |
| 5,697,373 A | 12/1997 | Richards-Kortum et al. | |
| 5,698,397 A | 12/1997 | Zarling et al. | |
| 5,710,630 A | 1/1998 | Essenpreis et al. | |
| 5,716,324 A | 2/1998 | Toida | |
| 5,719,399 A | 2/1998 | Alfano et al. | |
| 5,730,731 A | 3/1998 | Mollenauer et al. | |
| 5,735,276 A | 4/1998 | Lemelson | |
| 5,740,808 A | 4/1998 | Panescu et al. | |
| 5,748,318 A | 5/1998 | Maris et al. | |
| 5,748,598 A | 5/1998 | Swanson et al. | |
| 5,784,352 A | 7/1998 | Swanson et al. | |
| 5,785,651 A | 7/1998 | Kuhn et al. | |
| 5,795,295 A | 8/1998 | Hellmuth et al. | |
| 5,801,826 A | 9/1998 | Williams | |
| 5,801,831 A | 9/1998 | Sargoytchev et al. | |
| 5,803,082 A | 9/1998 | Stapleton et al. | |
| 5,807,261 A | 9/1998 | Benaron et al. | |
| 5,810,719 A | 9/1998 | Toida | |
| 5,817,144 A | 10/1998 | Kenton et al. | |
| 5,836,877 A | 11/1998 | Zavislan et al. | |
| 5,840,023 A | 11/1998 | Oraevsky et al. | |
| 5,840,075 A | 11/1998 | Mueller et al. | |
| 5,842,995 A | 12/1998 | Mahadevan-Jansen et al. | |
| 5,843,000 A | 12/1998 | Nishioka et al. | |
| 5,843,052 A | 12/1998 | Benja-Athon | |
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,910,839 A | 6/1999 | Erskine et al. | |
| 5,912,764 A | 6/1999 | Togino | |
| 5,920,373 A | 7/1999 | Bille | |
| 5,920,390 A | 7/1999 | Farahi et al. | |
| 5,921,926 A | 7/1999 | Rolland et al. | |
| 5,926,592 A | 7/1999 | Harris et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |
| 5,968,064 A | 10/1999 | Selmon et al. | |
| 5,975,697 A | 11/1999 | Podoleanu et al. | |
| 5,983,125 A | 11/1999 | Alfano et al. | |
| 5,987,346 A | 11/1999 | Benaron et al. | |
| 5,991,697 A | 11/1999 | Nelson et al. | |
| 5,994,690 A | 11/1999 | Kulkarni et al. | |
| 5,995,223 A | 11/1999 | Power | |
| 6,002,480 A | 12/1999 | Izatt et al. | |
| 6,004,314 A | 12/1999 | Wei et al. | |
| 6,006,128 A | 12/1999 | Izatt et al. | |
| 6,007,996 A | 12/1999 | McNamara et al. | |

| Patent No. | Date | Inventor |
|---|---|---|
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | DiMarzio et al. |
| 6,033,721 A | 3/2000 | Nassuphis |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,496 A | 7/2000 | Hill |
| 6,091,984 A | 7/2000 | Perelman et al. |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A * | 10/2000 | Tearney et al. ............... 356/479 |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,517,532 B1 | 2/2003 | Altshuler et al. |
| 6,538,817 B1 | 3/2003 | Farmer et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,564,087 B1 | 5/2003 | Pitris et al. |
| 6,564,089 B2 | 5/2003 | Izatt et al. |
| 6,567,585 B2 | 5/2003 | Harris |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,701,181 B2 | 3/2004 | Tang et al. |
| 6,721,094 B1 | 4/2004 | Sinclair et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,190,464 B2 | 3/2007 | Alphonse |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,609,391 B2 | 10/2009 | Betzig |
| 7,646,905 B2 | 1/2010 | Guittet et al. |
| 7,664,300 B2 | 2/2010 | Lange et al. |
| 7,805,034 B2 | 9/2010 | Kato et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Eateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0122246 A1* | 9/2002 | Tearney et al. ............... 359/368 |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |

| | | |
|---|---|---|
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0053673 A1 | 3/2003 | Dewaele et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0077949 A1 | 4/2004 | Blofgett et al. |
| 2004/0086245 A1 | 5/2004 | Farroni et al. |
| 2004/0100631 A1 | 5/2004 | Bashkansky et al. |
| 2004/0100681 A1 | 5/2004 | Bjarklev et al. |
| 2004/0126048 A1 | 7/2004 | Dave et al. |
| 2004/0126120 A1* | 7/2004 | Cohen et al. ............... 398/158 |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0212808 A1 | 10/2004 | Okawa et al. |
| 2004/0239938 A1 | 12/2004 | Izatt |
| 2004/0246583 A1 | 12/2004 | Mueller et al. |
| 2004/0254474 A1 | 12/2004 | Seibel et al. |
| 2004/0263843 A1 | 12/2004 | Knopp et al. |
| 2005/0004453 A1* | 1/2005 | Tearney et al. ............ 600/427 |
| 2005/0018133 A1 | 1/2005 | Huang et al. |
| 2005/0018201 A1 | 1/2005 | De Boer et al. |
| 2005/0035295 A1 | 2/2005 | Bouma et al. |
| 2005/0046837 A1 | 3/2005 | Izumi et al. |
| 2005/0057680 A1 | 3/2005 | Agan |
| 2005/0057756 A1 | 3/2005 | Fang et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2006/0103850 A1 | 5/2006 | Alphonse et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0184048 A1 | 8/2006 | Saadat et al. |
| 2006/0193352 A1 | 8/2006 | Chong et al. |
| 2006/0244973 A1 | 11/2006 | Yun et al. |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0086013 A1 | 4/2007 | De Lega et al. |
| 2007/0133002 A1 | 6/2007 | Wax et al. |
| 2007/0188855 A1 | 8/2007 | Shishkov et al. |
| 2007/0223006 A1 | 9/2007 | Tearney et al. |
| 2007/0236700 A1 | 10/2007 | Yun et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0049220 A1 | 2/2008 | Izzia et al. |
| 2008/0097225 A1 | 4/2008 | Tearney et al. |
| 2008/0228086 A1 | 9/2008 | Ilegbusi et al. |
| 2009/0273777 A1 | 11/2009 | Yun et al. |

FOREIGN PATENT DOCUMENTS

| | | |
|---|---|---|
| DE | 4309056 | 9/1994 |
| DE | 19542955 | 5/1997 |
| DE | 10351319 | 5/2005 |
| EP | 0110201 | 6/1984 |
| EP | 0251062 | 1/1988 |
| EP | 0590268 | 4/1994 |
| EP | 0617286 | 2/1995 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 20040056907 | 2/1992 |
| JP | 413555 | 5/1992 |
| JP | 4135550 | 5/1992 |
| JP | 5509417 | 11/1993 |
| JP | 02214127 | 7/2002 |
| JP | 20030035659 | 2/2003 |
| JP | 2007271761 | 10/2007 |
| WO | 7900841 | 10/1979 |
| WO | 9216865 | 10/1992 |
| WO | 2006039091 | 10/1992 |
| WO | 9219930 | 11/1992 |
| WO | 9201966 | 2/1993 |
| WO | 9303672 | 3/1993 |
| WO | 9216865 | 10/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9848846 | 11/1998 |
| WO | 9905487 | 2/1999 |
| WO | 9944089 | 2/1999 |
| WO | 9944089 | 9/1999 |
| WO | 9957507 | 11/1999 |
| WO | 0058766 | 10/2000 |
| WO | 0101111 | 1/2001 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0237075 | 5/2002 |
| WO | 0238040 | 5/2002 |
| WO | 02053050 | 7/2002 |
| WO | 02054027 | 7/2002 |
| WO | 02084263 | 10/2002 |
| WO | 03013624 | 2/2003 |
| WO | 03030119 | 3/2003 |
| WO | 03046495 | 6/2003 |
| WO | 03046636 | 6/2003 |
| WO | 03062478 | 6/2003 |
| WO | 0353226 | 7/2003 |
| WO | 03062802 | 7/2003 |
| WO | 03105678 | 12/2003 |
| WO | 2004034869 | 4/2004 |
| WO | 2004057266 | 7/2004 |
| WO | 2004066824 | 8/2004 |
| WO | 2004088361 | 10/2004 |
| WO | 1550203 | 12/2004 |
| WO | 2004105598 | 12/2004 |

| | | |
|---|---|---|
| WO | 2005000115 | 1/2005 |
| WO | 2005047813 | 5/2005 |
| WO | 2005054780 | 6/2005 |
| WO | 2005082225 | 9/2005 |
| WO | 2005004743 | 1/2006 |
| WO | 2006014392 | 2/2006 |
| WO | WO 2006/038876 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007083138 | 7/2007 |
| WO | 2007084995 | 7/2007 |

OTHER PUBLICATIONS

Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.

Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US Vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.

European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yagoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
Fujimoto et al., "High Resolution in Vivo Intra-Arterial Imaging with Optical Coherence Tomography," *Official Journal of the British Cardiac Society*, vol. 82, pp. 128-133 Heart, 1999.
D. Huang et al., "Optical Coherence Tomography," *Science*, vol. 254, pp. 1178-1181, Nov. 1991.
Tearney et al., "High-Speed Phase -and Group Delay Scanning with a Grating Based Phase Control Delay Line," *Optics Letters*, vol. 22, pp. 1811-1813, Dec. 1997.
Rollins, et al., "In Vivo Video Rate Optical Coherence Tomography," *Optics Express*, vol. 3, pp. 219-229, Sep. 1998.
Saxer, et al., High Speed Fiber-Based Polarization-Sensitive Optical Coherence Tomography of in Vivo Human Skin, *Optical Society of America*, vol. 25, pp. 1355-1357, Sep. 2000.
Oscar Eduardo Martinez, "3000 Times Grating Compress or with Positive Group Velocity Dispersion," *IEEE*, vol. QE-23, pp. 59-64, Jan. 1987.
Kulkarni, et al., "Image Enhancement in Optical Coherence Tomography Using Deconvolution," *Electronics Letters*, vol. 33, pp. 1365-1367, Jul. 1997.
Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Images," *Journal of Biomedical Optics*, vol. 4, pp. 125-136, Jan. 1999.
Tearney, et al., "In Vivo Endoscopic Optical Biopsy with Optical Coherence Tomography," *Science*, vol. 276, Jun. 1997.
W. Drexler et al., "In Vivo Ultrahigh-Resolution Optical Coherence Tomography," *Optics Letters* vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.
Andretzky, P. et al., "Optical Coherence Tomography by Spectral Radar: Improvement of Signal-to-Noise Ratio," *The International Society for Optical Engineering*, USA, vol. 3915, 2000.
Ballif, J. et al., "Rapid and Scalable Scans at 21 m/s in optical Low-Coherence Reflectometry," *Optics Letters*, vol. 22, pp. 757-759, Jun. 1997.
Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.
Beaud, P. et al., "Optical Reflectometry with Micrometer Resolution for the Investigation of Integrated Optical-Devices," *Leee Journal of Quantum Electronics*, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.
Brinkmeyer, E. et al., "Efficient Algorithm or Non-Equidistant Interpolation of Sampled Data," *Electronics Letters*, vol. 28, p. 693, Mar. 1992.
Brinkmeyer, E. et al., "High-Resolution OCDR in Dispersive Wave-Guides," *Electronics Letters*, vol. 26, pp. 413-414, Mar. 1990.
Chinn, S.R. et al., "Optical Coherence Tomography Using a Frequency-Tunable Optical Source," *Optics Letters*, vol. 22, pp. 340-342, Mar. 1997.
Danielson, B.L. et al., "Absolute Optical Ranging Using Low Coherence Interferometry," *Applied Optics*, vol. 30, p. 2975, Jul. 1991.
Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.
Eickhoff, W. et al., "Optical Frequency-Domain Reflectometry in Single-Mode Fiber," *Applied Physics Letters*, vol. 39, pp. 693-695, 1981.
Fercher, Adolf "Optical Coherence Tomography," *Journal of Biomedical Optics*, vol. 1, pp. 157-173, Apr. 1996.
Ferreira, L.A. et al., "Polarization-Insensitive Fiberoptic White-Light Interferometry," *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.
Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol.22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and.Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*,vol. 36, pp. 6548-6553, Sep. 1997.

Mitsui, Takahisa, "Dynamic Range of Optical Reflectometry with Spectral Interferometry," *Japanese Journal of Applied Physics Part 1—Regular Papers Short Notes & Review Papers*, vol.38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.Sorin, W. V. et al., "A Simple Intensity Noise-Reduction Technique for Optical Coherence Reflectometry," IEEE Photonics Technology Letters, Vol. 4, pp. Low-1404-1406,.Dec. 1992.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of LightwaveTechnology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No.25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17,.Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of in Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," Optics Letters, vol. 28, No. 19, Oct. 1, 2003, pp. 1775-1777.

Yang, Ying et al., "Observations of Birefringence in Tissues from Optic-Fibre-Based Optical Coherence Tomography," Measurement Science and Technology, Nov. 2002, pp. 41-46.

Yun, S.H. et al., "High-Speed Optical Frequency-Domain Imaging," Optics Express, vol. 11, No. 22, Nov. 3, 2003, pp. 2953-2963.

Yun, S.H. et al., "High-Speed Spectral-Domain Optical Coherence Tomography at 1.3 μm Wavelength," Optics Express, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," Optics Express, vol. 11, No. 24, Dec. 1, 2003, pp. 3262-3270.

Pircher, Michael et al., "Three Dimensional Polarization Sensitive OCT of Human Skin in Vivo," 2004, Optical Society of America.

Götzinger, Erich et al., "Measurement and Imaging of Birefringent Properties of the Human Cornea with Phase-Resolved, Polarization-Sensitive Optical Coherence Tomography," Journal of Biomedical Optics, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," Optics Letters, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," Investigative Ophthalmology & Visual Science, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," Physics in Medicine and Biology, 2004, pp. 1295-1306.

Nassif, Nader et al., "In Vivo Human Retinal Imaging by Ultrahigh-Speed Spectral Domain Optical Coherence Tomography," Optics Letters, vol. 29, No. 5, Mar. 1, 2004, pp. 480-482.

Nassif, N. A. et al., "In Vivo High-Resolution Video-Rate Spectral-Domain Optic Coherence Tomography of the Human Retina and Optic Nerve," Optics Express, vol. 12, No. 3, Feb. 9, 2004, pp. 367-376.

Park, B. Hyle et al., "Comment on Optical-Fiber-Based Mueller Optical Coherence Tomography," Optics Letters, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," Optics Letters, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," Elsevier, Burns, 2004, pp. 511-517.

Pierce, Mark C. et al., "Advances in Optical Coherence Tomography Imaging for Dermatology," The Society for Investigative Dermatology, Inc. 2004, pp. for 458-463.

Pierce, Mark C. et al., "Birefringence Measurements in Human Skin Using Polarization-Sensitive Optical Coherence Tomography," Journal of Biomedical Optics, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," Journal of Biomedical Optics, vol. 9, No. 1, Jan./Feb. 2004, pp. 121-125.

Pircher, Michael et al., "Imaging of Polarization Properties of Human Retina in Vivo with Phase Resolved Transversal PS-OCT," Optics Express, vol. 12, No. 24, Nov. 29, 2004 pp. 5940-5951.

Pircher, Michael et al., "Transversal Phase Resolved Polarization Sensitive Optical Coherence Tomography," Physics in Medicine & Biology, 2004, pp. 1257-1263.

Srinivas, Shyam M. et al., "Determination of Burn Depth by Polarization-Sensitive Optical Coherence Tomography," Journal of Biomedical Optics, vol. 9, No. 1, Jan./Feb. 2004, pp. 207-212.

Strasswimmer, John et al., "Polarization-Sensitive Optical Coherence Tomography of Invasive Basal Cell Carcinoma," Journal of Biomedical Optics, vol. 9, No. 2, Mar./Apr. 2004, pp. 292-298.

Todorovič, Miloš et al., "Determination of Local Polarization Properties of Biological Samples in the Presence of Diattenuation by use of Mueller Optical Coherence Tomography," Optics Letters, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." Optics Letters 16(24): 1984-1986.

Aigouy, L., A. Lahrech, et al. (1999). "Polarization effects in apertureless scanning near-field optical microscopy: an experimental study." Optics Letters 24(4): 187-189.

Akiba, M., K. P. Chan, et al. (2003). "Full-field optical coherence tomography by two-dimensional heterodyne detection with a pair of CCD cameras." Optics Letters 28(10): 816-818.

Akkin, T., D. P. Dave, et al. (2004). "Detection of neural activity using phase-sensitive optical low-coherence reflectometry." Optics Express 12(11): 2377-2386.

Akkin, T., D. P. Dave, et al. (2003). "Surface analysis using phase sensitive optical low coherence reflectometry." Lasers in Surgery and Medicine: 4-4.

Akkin, T., D. P. Dave, et al. (2003). "Imaging tissue response to electrical and photothermal stimulation with nanometer sensitivity." Lasers in Surgery and Medicine 33(4): 219-225.

Akkin, T., T. E. Milner, et al. (2002). "Phase-sensitive measurement of birefringence change as an indication of neural functionality and diseases." Lasers in Surgery and Medicine: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." Proceedings of SPIE—The International Society for Optical Engineering 3567: pp. 78-87.

Antcliff, R. J., T. J. ffytche, et al. (2000). "Optical coherence tomography of melanocytoma." American Journal of Ophthalmology 130(6): 845-7.

Antcliff, R. J., M. R. Stanford, et al. (2000). "Comparison between optical coherence tomography and fundus fluorescein angiography for the detection of cystoid macular edema in patients with uveitis." Ophthalmology 107(3): 593-9.

Anvari, B., T. E. Milner, et al. (1995). "Selective Cooling of Biological Tissues—Application for Thermally Mediated Therapeutic Procedures." Physics in Medicine and Biology 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." Physics in Medicine and Biology 40(9): 1451-1465.

Arend, O., M. Ruffer, et al. (2000). "Macular circulation in patients with diabetes mellitus with and without arterial hypertension." British Journal of Ophthalmology 84(12): 1392-1396.

Arimoto, H. and Y. Ohtsuka (1997). "Measurements of the complex degree of spectral coherence by use of a wave-front-folded interferometer." Optics Letters 22(13): 958-960.

Azzolini, C., F. Patelli, et al. (2001). "Correlation between optical coherence tomography data and biomicroscopic interpretation of idiopathic macular hole." American Journal of Ophthalmology 132(3): 348-55.

Baba, T., K. Ohno-Matsui, et al. (2002). "Optical coherence tomography of choroidal neovascularization in high myopia." Acta Ophthalmoloqica Scandinavica 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." Proc. SPIE, 2925: p. 298-303.

Baney, D. M. and W. V. Sorin (1993). "Extended-Range Optical Low-Coherence Reflectometry Using a Recirculating Delay Technique." Ieee Photonics Technology Letters 5(9): 1109-1112.

Baney, D. M., B. Szafraniec, et al. (2002). "Coherent optical spectrum analyzer." Ieee Photonics Technology Letters 14(3): 355-357.

Barakat, R. (1981). "Bilinear Constraints between Elements of the 4by4 Mueller-Jones Transfer-Matrix of Polarization Theory." Optics Communications 38(3): 159-161.

Barakat, R. (1993). "Analytic Proofs of the Arago-Fresnel Laws for the Interference of Polarized-Light." Journal of the Optical Society of America a-Optics Image Science and Vision 10(1): 180-185.

Barbastathis, G. and D. J. Brady (1999). "Multidimensional tomographic imaging using volume holography." Proceedings of the Ieee 87(12): 2098-2120.

Bardal, S., A. Kamal, et al. (1992). "Photoinduced Birefringence in Optical Fibers—a Comparative-Study of Low-Birefringence and High-Birefringence Fibers." Optics Letters 17(6): 411-413.

Barsky, S. H., S. Rosen, et al. (1980). "Nature and Evolution of Port Wine Stains—Computer-Assisted Study." Journal of Investigative Dermatology 74(3): 154-157.

Barton, J. K., J. A. Izatt, et al. (1999). "Three-dimensional reconstruction of blood vessels from in vivo color Doppler optical coherence tomography images." Dermatology 198(4): 355-361.

Barton, J. K., A. Rollins, et al. (2001). "Photothermal coagulation of blood vessels: a comparison of high-speed optical coherence tomography and numerical modelling." Physics in Medicine and Biology 46.

Barton, J. K., A. J. Welch, et al. (1998). "Investigating pulsed dye laser-blood vessel interaction with color Doppler optical coherence tomography." Optics Express 3.

Bashkansky, M., M. D. Duncan, et al. (1997). "Subsurface defect detection in ceramics by high-speed high-resolution optical coherent tomography." Optics Letters 22 (1):61-63.

Bashkansky, M. and J. Reintjes (2000). "Statistics and reduction of speckle in optical coherence tomography." Optics Letters 25(8): 545-547.

Baumgartner, A., S. Dichtl, et al. (2000). "Polarization-sensitive optical coherence tomography of dental structures." Caries Research 34(1): 59-69.

Baumgartner, A., C. K. Hitzenberger, et al. (2000). "Resolution-improved dual-beam and standard optical coherence tomography: a comparison." Graefes Archive for Clinical and Experimental Ophthalmology 238(5): 385-392.

Baumgartner, A., C. K. Hitzenberger, et at. (1998) "Signal and resolution enhancements in dual beam optical coherence tomography of the human eye." Journal of Biomedical Optics 3(1): 45-54.

Beaurepaire, E., P. Gleyzes, et at. (1998). Optical coherence microscopy for the in-depth study of biological structures: System based on a parallel detection scheme, Proceedings of SPIE—The International Society for Optical Engineering.

Beaurepaire, E., L. Moreaux, et al. (1999). "Combined scanning optical coherence and two-photon-excited fluorescence microscopy." Optics Letters 24(14): 969-971.

Bechara, F. G., T. Gambichler, et al. (2004). "Histomorphologic correlation with routine histology and optical coherence tomography." Skin Research and Technology 10 (3): 169-173.

Bechmann, M., M. J. Thiel, et al. (2000). "Central corneal thickness determined with optical coherence tomography in various types of glaucoma. [see comments]." British Journal of Ophthalmology 84(11): 1233-7.

Bek, T. and M. Kandi (2000). "Quantitative anomaloscopy and optical coherence tomography scanning in central serous chorioretinopathy." Acta Ophthalmologica Scandinavica 78(6): 632-7.

Benoit, A. M., K. Naoun, et al. (2001). "Linear dichroism of the retinal nerve fiber layer expressed with Mueller matrices." Applied Optics 40(4): 565-569.

Bicout, D., C. Brosseau, et al. (1994). "Depolarization of Multiply Scattered Waves by Spherical Diffusers—Influence of the Size Parameter." Physical Review E 49(2): 1767-1770.

Blanchot, L., M. Lebec, et al. (1997). Low-coherence in depth microscopy for biological tissues imaging: Design of a real time control system. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." Survey of Ophthalmology 45(Suppl 3): S305-12; discussion S332-4.

Blumenthal, E. Z., J. M. Williams, et al. (2000). "Reproducibility of nerve fiber layer thickness measurements by use of optical coherence tomography." Ophthalmology 107(12): 2278-82.

Boppart, S. A., B. E. Bouma, et al. (1996). "Imaging developing neural morphology using optical coherence tomography." Journal of Neuroscience Methods 70.

Boppart, S. A., B. E. Bouma, et al. (1997). "Forward-imaging instruments for optical coherence tomography." Optics Letters 22.

Boppart, S. A., B. E. Bouma, et al. (1998). "Intraoperative assessment of microsurgery with three-dimensional optical coherence tomography." Radiology 208: 81-86.

Boppart, S. A., J. Herrmann, et al. (1999). "High-resolution optical coherence tomography-guided laser ablation of surgical tissue." Journal of Surgical Research 82(2): 275-84.

Bouma, B. E. and J. G. Fujimoto (1996). "Compact Kerr-lens mode-locked resonators." Optics Letters 21. 134-136.

Bouma, B. E., L. E. Nelson, et al. (1998). "Optical coherence tomographic imaging of human tissue at 1.55 mu m and 1.81 mu m using Er and Tm-doped fiber sources." Journal of Biomedical Optics 3. 76-79.

Bouma, B. E., M. Ramaswamy-Paye, et al. (1997). "Compact resonator designs for mode-locked solid-state lasers." Applied Physics B (Lasers and Optics) B65. 213-220.

Bouma, B. E. and G. J. Tearney (2002). "Clinical imaging with optical coherence tomography." Academic Radiology 9(8): 942-953.

Bouma, B. E., G. J. Tearney, et al. (1996). "Self-phase-modulated Kerr-lens mode-locked Cr:forsterite laser source for optical coherence tomography." Optics Letters 21(22): 1839.

Bouma, B. E., G. J. Tearney, et al. (2000). "High-resolution imaging of the human esophagus and stomach in vivo using optical coherence tomography." Gastrointestinal Endoscopy 51(4): 467-474.

Bouma, B. E., G. J. Tearney, et al. (2003). "Evaluation of intracoronary stenting by intravascular optical coherence tomography." Heart 89(3): 317-320.

Bourquin, S., V. Monterosso, et al. (2000). "Video-rate optical low-coherence reflectometry based on a linear smart detector array." Optics Letters 25(2): 102-104.

Bourquin, S., P. Seitz, et al. (2001). "Optical coherence topography based on a two-dimensional smart detector array." Optics Letters 26(8): 512-514.

Bouzid, A., M. A. G. Abushagur, et al. (1995). "Fiber-optic four-detector polarimeter." Optics Communications 118(3-4): 329-334.

Bowd, C., R. N. Weinreb, et al. (2000). "The retinal nerve fiber layer thickness in ocular hypertensive, normal, and glaucomatous eyes with optical coherence tomography." Archives of Ophthalmology 118(1): 22-6.

Bowd, C., L. M. Zangwill, et al. (2001). "Detecting early glaucoma by assessment of retinal nerve fiber layer thickness and visual function." Investigative Ophthalmology & Visual Science 42(9): 1993-2003.

Bowd, C., L. M. Zangwill, et al. (2002). "Imaging of the optic disc and retinal nerve fiber layer: the effects of age, optic disc area, refractive error, and gender." Journal of the Optical Society of America, A, Optics, Image Science, & Vision 19(1): 197-207.

Brand, S., J. M. Poneros, et al. (2000). "Optical coherence tomography in the gastrointestinal tract." Endoscopy 32(10): 796-803.

Brezinski, M. E. and J. G. Fujimoto (1999). "Optical coherence tomography: high-resolution imaging in nontransparent tissue." IEEE Journal of Selected Topics in Quantum Electronics 5(4): 1185-1192.

Brezinski, M. E., G. J. Tearney, et al. (1996). "Imaging of coronary artery microstructure (in vitro) with optical coherence tomography." American Journal of Cardiology 77 (1): 92-93.

Brezinski, M. E., G. J. Teamey, et al. (1996). "Optical coherence tomography for optical biopsy—Properties and demonstration of vascular pathology." Circulation 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in the Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectomerry with Micrometer Resolution." *Applied Optics* 26(14): 2836-2842.

Dave, D. P. and T. E. Milner (2000). "Doppler-angle measurement in highly scattenng media." *Optics Letters* 5(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling ot White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. K., A. H. O. Karkkainen, et al. (2002). "Toward the development ot miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002)."Real-time phase-resolved optical coherence tomography and optical Doppler tomography." *Optics Express* 10(5): 236-245.

Dobrin, P. B. (1996). "Effect of histologic preparation on the cross-sectional area ot arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hilzenberger, et al. (1998). "Investigation of dispersion effects in ocular media by multiple wavelength partial coherence interferometry." *Experimental Eye Research* 66(1): 25-33.

Drexler, W., C. K. Hilzenberger, et al. (1996). "(Sub)micrometer precision biometry oi the human eye by optical coherence tomography and topography." *Investigative Ophthalmology & Visual Science* 37(3): 4374-4374.

Drexler, W., C. K. Hitzenberger, et al. (1995). "Measurement of the Thickness ot Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography, [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-held optical coherence tomography with a Linnik microscope." *Applied Optics* 41(4): 805-812.

Ducros, M, M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method tor objective determination of burn depth." *Burns* 25(8): 697-704.

Elbaum, M, M. King, et al. (1972). "Wavelength-Diversity Technique for Reduction of Speckle Size." *Journal of the Optical Society of America* 62(5): 732-&.

Ervin, J. C, H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and son tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro- Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hilzenberger, et al. (1996). *Ocular partial coherence interferometry*. Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation tor Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth- scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C, F. Bruyere, et al. (1998)."PMD second-order effects on pulse propagation in single-mode optical fibers." *Ieee Photonics Technology Letters* 10(12): 1739-1741

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Charactenstic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6(1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al (2003) "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6):869-874.

Gordon, M. O. and M. A. Kass (1999). "The Ocular Hypertension Treatment study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, el al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated User Interferometric Ellipsometry and Precision Reflectomerry." *Journal of Physics E-Scientific Instruments* 16(7): 654-661.

He. Z. Y., N. Mukohzaka, et al. (1997). "Srlective image extraction by synthesis of the coherence function using two-dimensional optical lock-in amplifier with microchannel spatial light modulator." *Ieee Photonics Technology Letters* 9(4): 514-516.

Hee. M. R., J. A. Izatt, et al. (1993). "Femtosecond Transillumination Optical Coherence Tomography." *Optics Letters* 18(12): 950-952.

Hee, M R., J. A. Izatt. et al. (1995) "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with oplical coherence tomography." *Archives of Ophthalmology* 113(8): 1019-29.

Hellmulh. T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, el al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K, A. Baumgartner, et al. (1999). "Dispersion effects in partial coherence interferometry: Implications for intraocular ranging." *Journal of Biomedical Optics* 4(1): 144-151.

Hilzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superlumincscent diodes." *Journal of Modern Optics* 46(12): 1763-1774.

Hitzenberger. C. K. and A. F. Fercher (1999). "Differential phase contrast in optical coherence tomography." *Optics Letters* 24(9): 622-624.

Hitzenberger, C. K., M. Sticker, et al. (2001). "Diflerenlial phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann. K., M. Happe, et al. (1998). "Optical coherence tomography (OCT) in dermatology." *Journal of Investigative Dermatology* 110(4): 583-583.

Hoh. S. T., D. S. Greenfield, et al. (2000). "Optical coherence tomography and scanning laser polarimetry in normal, ocular hypertensive, and glaucomatous eyes." *American Journal of Ophthalmology* 129(2) 129-35

Hohenleutner, U., M. Hilbert, et al. (1995) "Epidermal Damage and Limited Coagulation Depth with the Flashlamp-Pumped Pulsed Dye-Laser—Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351 -364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging rmcropolanmeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9):2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group celay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10):1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, ct al. (2001). "Optical coherence tomography of fractional macular elevations in eyes with proliferative diabetic retinopathy, [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112(12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang. I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl.S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohneke theory of optical activity." *Journal of the Optical Society of America* 31 (7): 500-503.

Jones, R. C. (1941). "A new calculus for the treatment ot optical systems I. Description and discussion of the calculus." *Journal of the Optical Society of America* 31(7): 488-493.

Jones, R. C. (1942). "A new calculus for the treatment of optical systems. IV." *Journal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1 155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomography to confirm early closure of macular holes." *American Journal of Ophthalmology* 130(5): 675-6.

Kaufman, T., S. N. Lusthaus, el al. (1990). "Deep Partial Skin Thickness Burns—a Reproducible Animal-Model to Study Burn Wound-Healing." *Burns* 16(1): 13-16.

Kemp, N. J., J. Park, ct al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A Quigley, et al. (2000). "Number of ganglion cells in glaucoma eyes compared with threshold visual field tests in the same persons." *Investigative Ophthalmology & Visual Science* 41 (3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13) 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay. M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a CCD Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C, M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers. J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer. D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121 (9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." Proc. SPIE 4619: 16-21.

Leitgeb, R. A., W. Drexler, et al. (2004). "Ultrahigh resolution Fourier domain optical coherence tomography." Optics Express 12(10): 2156-2165.

Leitgeb, R. A., C. K. Hitzenberger, et al. (2003). "Phase-shifting algorithm to achieve high-speed long-depth-range probing by frequency-domain optical coherence tomography." Optics Letters 28(22): 2201-2203.

Leitgeb, R. A., L. Schmetterer, et al. (2003). "Real-time assessment of retinal blood flow with ultrafast acquisition by color Doppler Fourier domain optical coherence tomography." Optics Express 11(23): 3116-3121.

Leitgeb, R. A., L. Schmetterer, et al. (2004). "Real-time measurement of in vitro flow by Fourier-domain color Doppler optical coherence tomography." Optics Letters 29 (2): 171-173.

LeRoyBrehonnet, F. and B. LeJeune (1997). "Utilization of Mueller matrix formalism to obtain optical targets depolarization and polarization properties." Progress in Quantum Electronics 21(2):109-151.

Leske, M. C, A. M. Connell, et al. (1995). "Risk factors for open-angle glaucoma. The Barbados Eye Study, [see comments]." Archives of Ophthalmology 113(7): 918-24.

Leske, M. C, A. M. Connell, et al. (2001). "Incidence of open-angle glaucoma: the Barbados Eye Studies. The Barbados Eye Studies Group, [see comments]." Archives of Ophthalmology 119(1):89-95.

Leske, M. C., A. Heijl, et al. (1999). "Early Manifest Glaucoma Trial. Design and Baseline Data." Ophthalmology 106(11): 2144-2153.

Lewis, S. E., J. R. DeBoer, et al. (2005). "Sensitive, selective, and analytical improvements to a porous silicon gas sensor." Sensors and Actuators B: Chemical 110(1): 54-65.

Lexer, F., C. K. Hitzenberger, et al. (1999). "Dynamic coherent focus OCT with depth- independent transversal resolution." Journal of Modern Optics 46(3): 541-553.

Li, X., C. Chudoba, et al. (2000). "Imaging needle for optical coherence tomography." Optics Letters 25: 1520-1522.

Li, X., T. H. Ko, et al. (2001). "Intraluminal fiber-optic Doppler imaging catheter for structural and functional optical coherence tomography." Optics Letters 26: 1906-1908.

Liddington, M. I. and P. G. Shakespeare (1996). "Timing of the thermographic assessment of burns." Burns 22(1): 26-8.

Lindmo, T., D. J. Smithies, et al. (1998). "Accuracy and noise in optical Doppler tomography studied by Monte Carlo simulation." Physics in Medicine and Biology 43(10): 3045-3064.

Liu, J., X. Chen, et al. (1999). "New thermal wave aspects on burn evaluation of skin subjected to instantaneous heating." IEEE Transactions on Biomedical Engineering 46(4): 420-8.

Luke, D. G., R. McBride, et al. (1995). "Polarization mode dispersion minimization in fiber-wound piezoelectric cylinders." Optics Letters 20(24): 2550-2552.

MacNeill, B. D., I. K. Jang, et al. (2004). "Focal and multi-focal plaque distributions in patients with macrophage acute and stable presentations of coronary artery disease." Journal of the American College of Cardiology 44(5): 972-979.

Mahgerefteh, D. and C. R. Menyuk (1999). "Effect of first-order PMD compensation on the statistics of pulse broadening in a fiber with randomly varying birefringence." Ieee Photonics Technology Letters 11(3): 340-342.

Maitland, D. J. and J. T. Walsh, Jr. (1997). "Quantitative measurements of linear birefringence during heating of native collagen." Lasers in Surgery & Medicine 20 (3): 310-8.

Majaron, B., S. M. Srinivas, et al. (2000). "Deep coagulation of dermal collagen with repetitive Er : YAG laser irradiation." Lasers in Surgery and Medicine 26(2): 215-222.

Mansuripur, M. (1991). "Effects of High-Numerical-Aperture Focusing on the State of Polarization in Optical and Magnetooptic Data-Storage Systems." Applied Optics 30(22): 3154-3162.

Marshall, G. W., S. J. Marshall, et al. (1997). "The dentin substrate: structure and properties related to bonding." Journal of Dentistry 25(6): 441-458.

Martin, P. (1997). "Wound healing—Aiming for perfect skin regeneration." Science 276 (5309): 75-81.

Martinez, O. E. (1987). "3000 Times Grating Compressor with Positive Group-Velocity Dispersion—Application to Fiber Compensation in 1.3-1.6 Mu-M Region." Ieee Journal of Quantum Electronics 23(1): 59-64.

Martinez, O. E., J. P. Gordon, et al. (1984). "Negative Group-Velocity Dispersion Using Refraction." Journal of the Optical Society of America a-Optics Image Science and Vision 1(10): 1003-1006.

McKinney, J. D., M. A. Webster, et al. (2000). "Characterization and imaging in optically scattering media by use of laser speckle and a variable-coherence source." Optics Letters 25(1): 4-6.

Miglior, S., M. Casula, et al. (2001). "Clinical ability of Heidelberg retinal tomograph examination to detect glaucomatous visual field changes." Ophthalmology 108 (9): 1621-7.

Milner, T. E., D. M. Goodman, et al. (1996). "Imaging laser heated subsurface chromophores in biological materials: Determination of lateral physical dimensions." Physics in Medicine and Biology 41(1): 31-44. .

Milner, T. E., D. M. Goodman, et al. (1995). "Depth Profiling of Laser-Heated Chromophores in Biological Tissues by Pulsed Photothermal Radiometry." Journal of the Optical Society of America a-Optics Image Science and Vision 12 (7): 1479-1488.

Milner, T. E., D. J. Smithies, et al. (1996). "Depth determination of chromophores in human skin by pulsed photothermal radiometry." Applied Optics 35(19): 3379-3385.

Mishchenko, M. I. and J. W. Hovenier (1995). "Depolarization of Light Backscattered by Randomly Oriented Nonspherical Particles." Optics Letters 20(12): 1356-&.

Mistlberger, A., J. M. Liebmann, et al. (1999). "Heidelberg retina tomography and optical coherence tomography in normal, ocular-hypertensive, and glaucomatous eyes." Ophthalmology 106(10): 2027-32.

Mitsui, T. (1999). "High-speed detection of ballistic photons propagating through suspensions using spectral interferometry." Japanese Journal of Applied Physics Part 1—Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." Ophthalmology 106(9): 1742-50.

Morgner, U., W. Drexler, et al. (2000). "Spectroscopic optical coherence tomography." Optics Letters 25(2): 111-113.

Morgner, U., F. X. Kartner, et al. (1999). "Sub-two-cycle pulses from a Kerr-lens mode-locked Ti : sapphire laser (vol. 24, p. 411, 1999)." Optics Letters 24(13): 920-920.

Mourant, J. R., A. H. Hielscher, et al. (1998). "Evidence of intrinsic differences in the light scattering properties of tumorigenic and nontumorigenic cells." Cancer Cytopathology 84(6): 366-374.

Muller, M., J. Squier, et al. (1998). "Dispersion pre-compensation of 15 femtosecond optical pulses for high-numerical-aperture objectives." Journal of Microscopy-Oxford 191: 141-150.

Muscat, S., N. McKay, et al. (2002). "Repeatability and reproducibility of corneal thickness measurements by optical coherence tomography." Investigative Ophthalmology & Visual Science 43(6): 1791-5.

Musch, D. C., P. R. Lichter, et al. (1999). "The Collaborative Initial Glaucoma Treatment Study. Study Design, Methods, and Baseline Characteristics of Enrolled Patients." Ophthalmology 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." Journal of Biomedical Optics 9(2): 274-281.

Nelson, J. S., K. M. Kelly, et al. (2001). "Imaging blood flow in human port-wine stain in situ and in real time using optical Doppler tomography." Archives of Dermatology 137(6): 741-744.

Newson, T. P., F. Farahi, et al. (1988). "Combined Interferometric and Polarimetric Fiber Optic Temperature Sensor with a Short Coherence Length Source." Optics Communications 68(3): 161-165.

November, L. J. (1993). "Recovery of the Matrix Operators in the Similarity and Congruency Transformations—Applications in Polarimetry." Journal of the Optical Society of America a-Optics Image Science and Vision 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678- 680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multifunctional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence in tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy."

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J.,T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interfcromctric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-lime, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, el al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11):2404-2422.

Wong, B. J. F., Y. H. Zhao, et al. (2004). "Imaging the internal structure of the rat cochlea using opilcal coherence tomography at 0.827 mu m and 1.3 mu m." *Otolaryngology-Head and Neck Surgery* 130(3): 334-338.

Yabushita, H. B., B.E.; Houser. S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10):686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." *Optics Communications* 208(4-6):209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13): 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomograpiy." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral-domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun. S. H., G. J Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25( 18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers" *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 73 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed. Biochim. Acta*, 1986,45(1/2):S 23-S 27.

T. Yoshimura et al., "Statistical propertiesof dynamic speckles", *J. Opt. Soc. Am A.* 1986, 3(7):1032-1054

Zimnyakov et al., "Spatial speckle correlometry in applicalions to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.
N.V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", Phys. Med. Biol. 2000(45): 1495-1509.
S.B. Adams Jr. et al., "The use of polarization sensitive optical coherence tomography and elastography to assess connective tissue", Optical Soc. of American Washington 2002, p. 3.
International Search Report for International Patent application No. PCT/US2005/039740.
International Written Opinion for International Patent application No. PCT/US2005/039740.
International Search Report for International Patent application No. PCT/US200S/030294.
International Written Opinion for International Patent application No. PCT/US200S/043951.
International Search Report for International Patent application No. PCT/US2005/043951.
Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664.
International Written Opinion for International Patent application No. PCT/US2005/023664.
Tearney et al., "Spectrally encoded miniature endoscopy" Optical Society of America; Optical Letters vol. 27, No. 6. Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704.
International Search Report for International Patent application No. PCT/US2004/039454.
International Written Opinion for International Patent application No. PCT/US2004/039454.
PCT International Preliminary Report on Patentability for International Application No. PCT/US2004/038404 dated Jun. 2, 2006.
Notice of Reasons for Rejection and English translation for Japanese Patent Application No. 2002-538830.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicene IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Applcation No. PCT/US2006/018865 filed May 5, 2006.
International Written Opinion for International Patent application No. PCT/US2006/018865 filed May 5,2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004,14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Writen Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstuction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastroenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No 4. pp. 659-667.
Reid, Brian J. (2001) "p53 and Neoplastic Progression in Barrett's Esophagus" *The American Journal of Gastroenterology* vol. 96, No. 5, p. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.
Kuipers E.J et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" *Gastrointestinal Endoscopy* vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.
Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol.57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med Biol* vol. 35, No. 9, pp. 1175-1209.

Anderson, R. Rox et al. (1983) "Selective Photothermolysis" Precise Microsurgery by Selective Absorption of Pulsed Radiation *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No.7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Office Action dated Oct. 11, 2007 for U.S. Appl. No. 11/534,095.

Office Action dated Oct. 9, 2007 for U.S. Appl. No. 09/709,162.

Notice of Allowance dated Oct. 3, 2007 for U.S. Appl. No. 11/225,840.

Siavash Yazdanfar et al., "In Vivo imaging in blood flow in human retinal vessels using color Doppler optical coherence tomography", SPIE, 1999 vol. 3598, pp. 177-184.

Office Action dated Oct. 30, 2007 for U.S. Appl. No. 11/670,069.

Tang C. L. et al., "Wide-band electro-optical tuning of semiconductor lasers", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

Telle M. John, et al., "New method for electro-optical tuning of tunable lasers", Applied Physics Letters, vol. 24, No. 2, Jan. 15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.

M. Gualini Muddassir et al., "Recent Advancements of Optical Interferometry Applied to Medicine", IEEE Transactions on Medical Imaging, vol. 23, No. 2, Feb. 2004, pp. 205-212.

Maurice L. Roch et al. "Noninvasive Vascular Elastography: Theoretical Framework", IEEE Transactions on Medical Imaging, vol. 23, No. 2, Feb. 2004, pp. 164-180.

Kirkpatrick J. Sean et al. "Optical Assessment of Tissue Mechanical Properties", Proceedings of the SPIE—The International Society for Optical Engineering SPIE—vol. 4001, 2000, pp. 92-101.

Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.

Parker K. J. et al., "Techniques for Elastic Imaging: A Review", IEEE Engineering in Medicine and Biology, Nov./Dec. 1996, pp. 52-59.

European Patent Office Search Report for Application No. 05791226.3.

Dubois Arnaud et al., "Ultrahigh-resolution OCT using white-light interference microscopy", Proceedings of SPIE, 2003, vol. 4956, pp. 14-21.

Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.

Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics.Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.

Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
W. Polkowski et al, (1998) "Clinical Decision making in Barrett's Oesophagus can be supported by Computerized Immunoquantitation and Morphometry of Features Associated with Proliferation and Differentiation," Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol, 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia -Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. Of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.

Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.

Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference"' IEEE Journal. Selected Topics in Quantum Electronics 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al. "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Extended European Search Report mailed Dec. 14, 2010 for EP 10182301.1.
Vaughn, J.M. et al., "Brillouin Scattering, Density and Elastic Properties of the Lens and Cornea of the Eye," Nature, vol. 284, Apr. 3, 1980, pp. 489-491.
Hess, S.T. et al., "Ultra High Resolution Imaging by Fluorescence Photoactivation Localization Microscopy," Biophysical Journal, vol. 91, Dec. 2006, pp. 4258-4272.
Fernandez Suarez, M. et al., "Fluorescent Probes for Super Resolution Imaging in Living Cells," Nature Reviews Molecular Cell Biology, vol. 9, Dec. 2008.

* cited by examiner

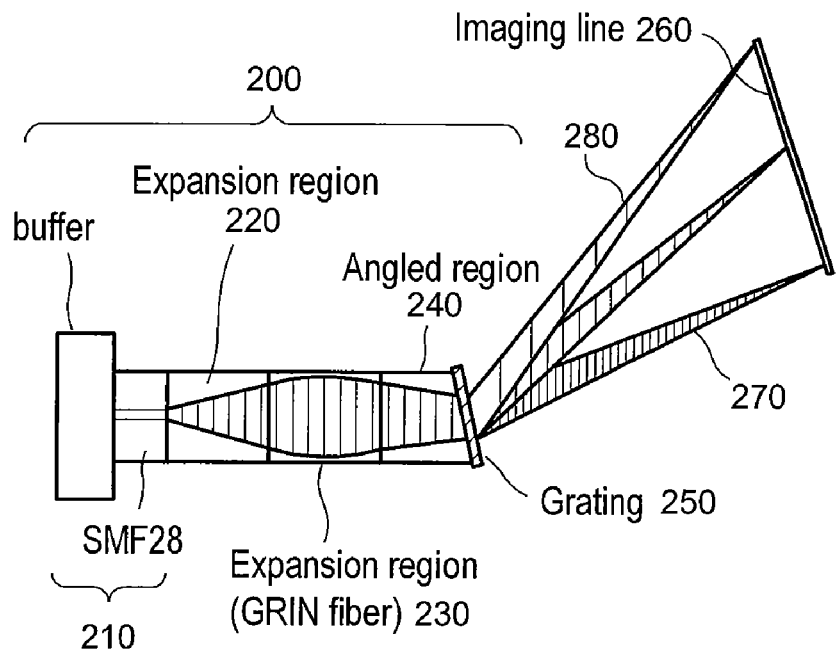
F I G. 2
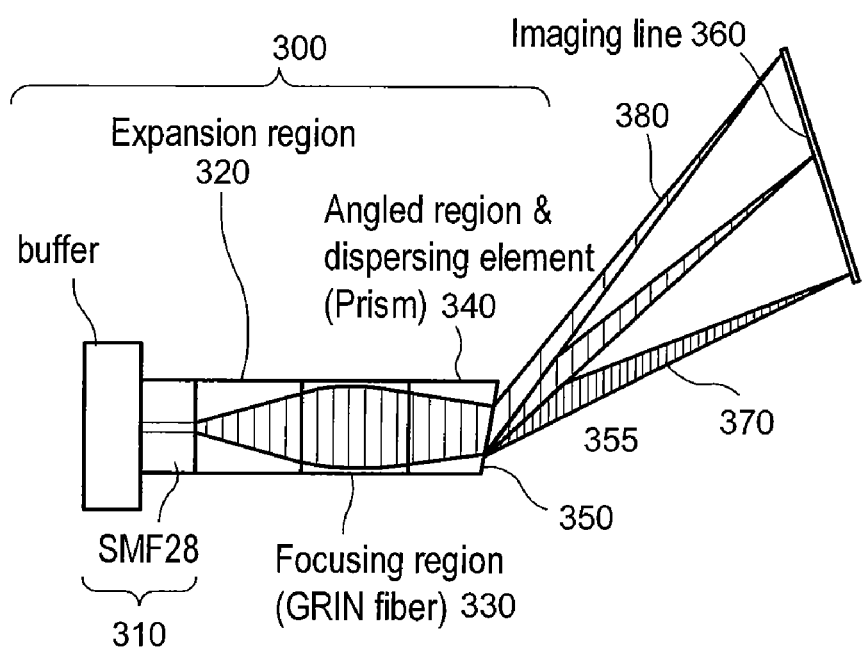
F I G. 3

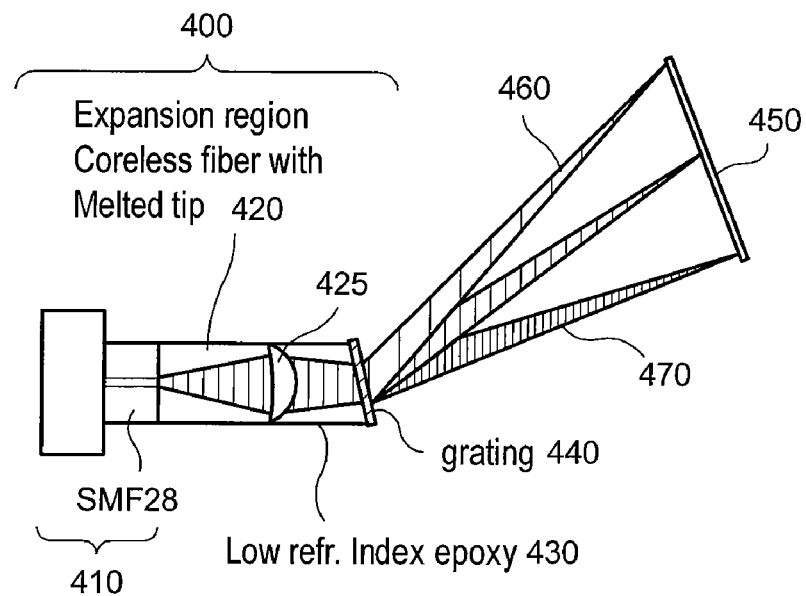
F I G. 4
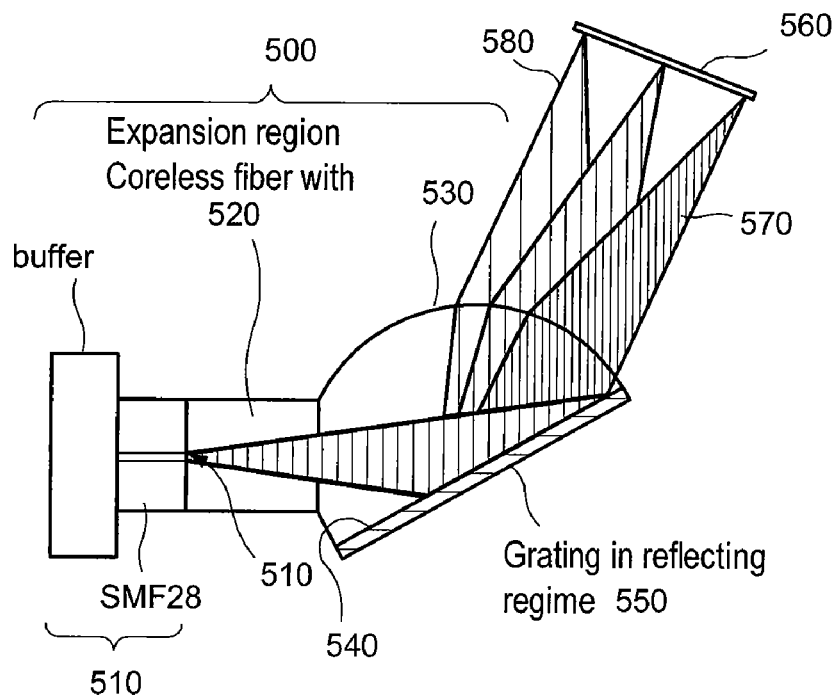
F I G. 5

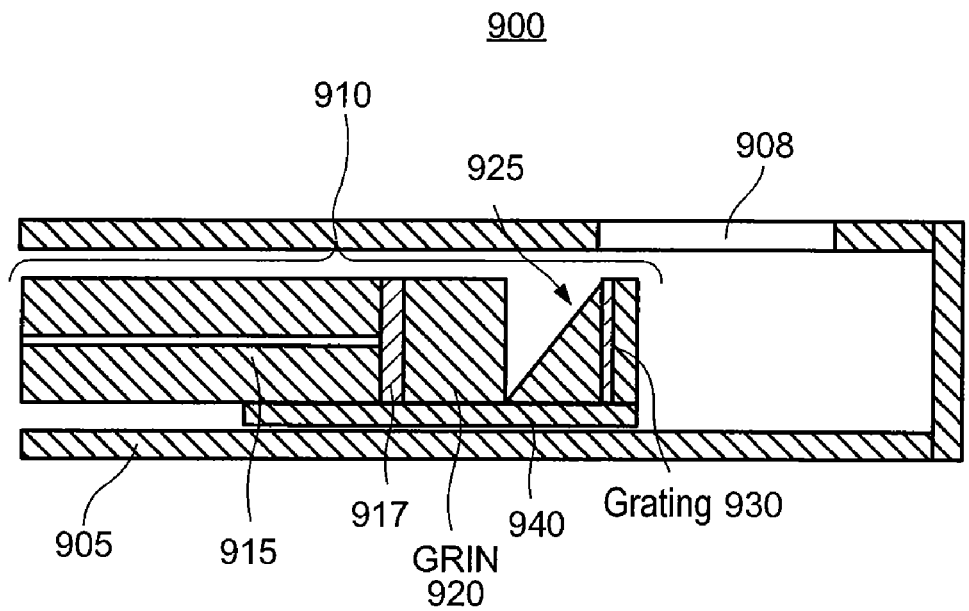
F I G. 9A
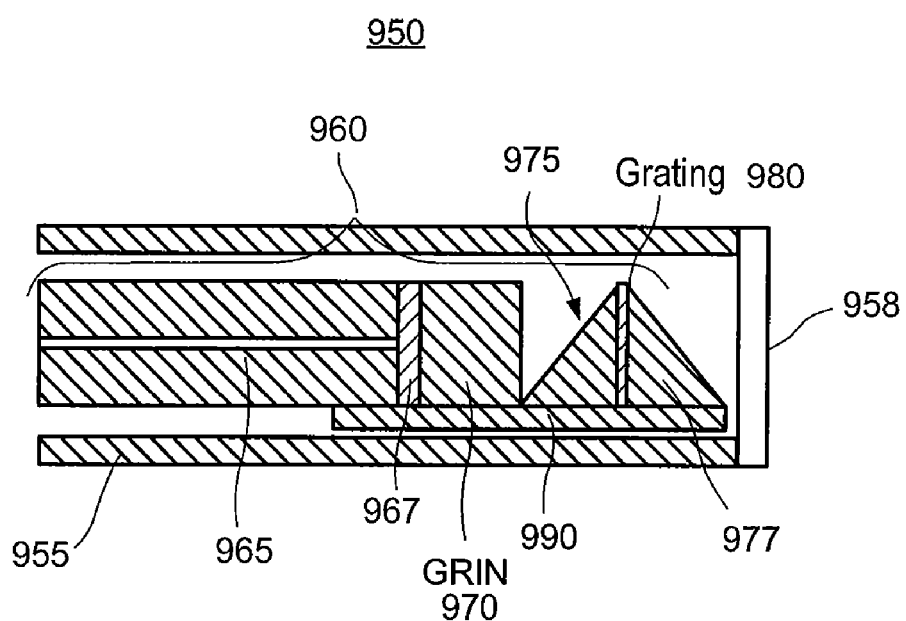
F I G. 9B

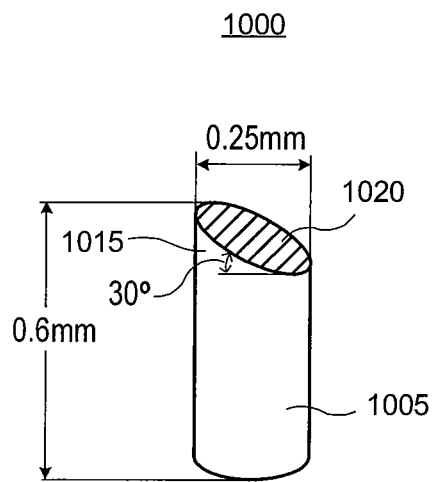
F I G. 10A
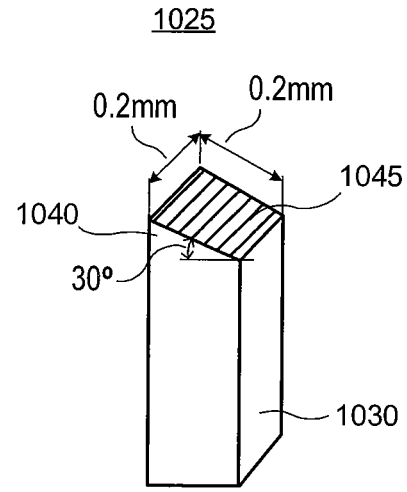
F I G. 10B
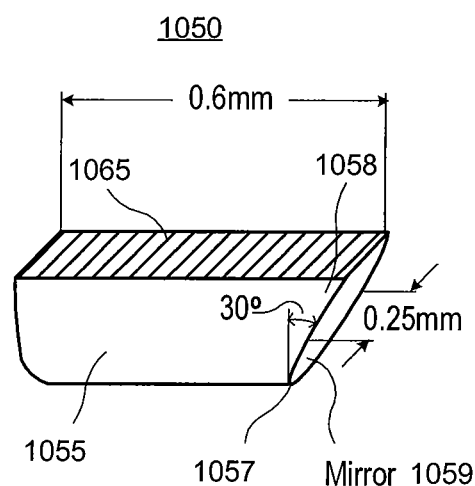
F I G. 10C
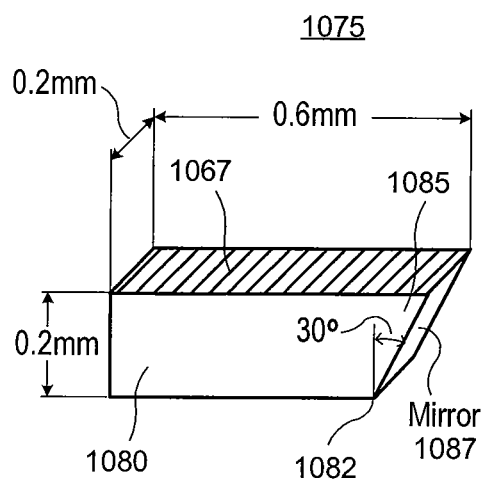
F I G. 10D

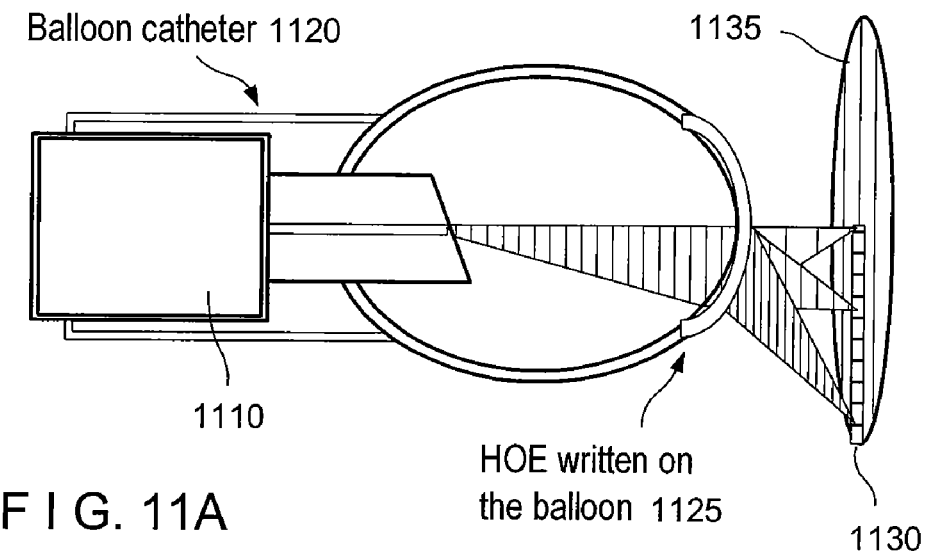
F I G. 11A
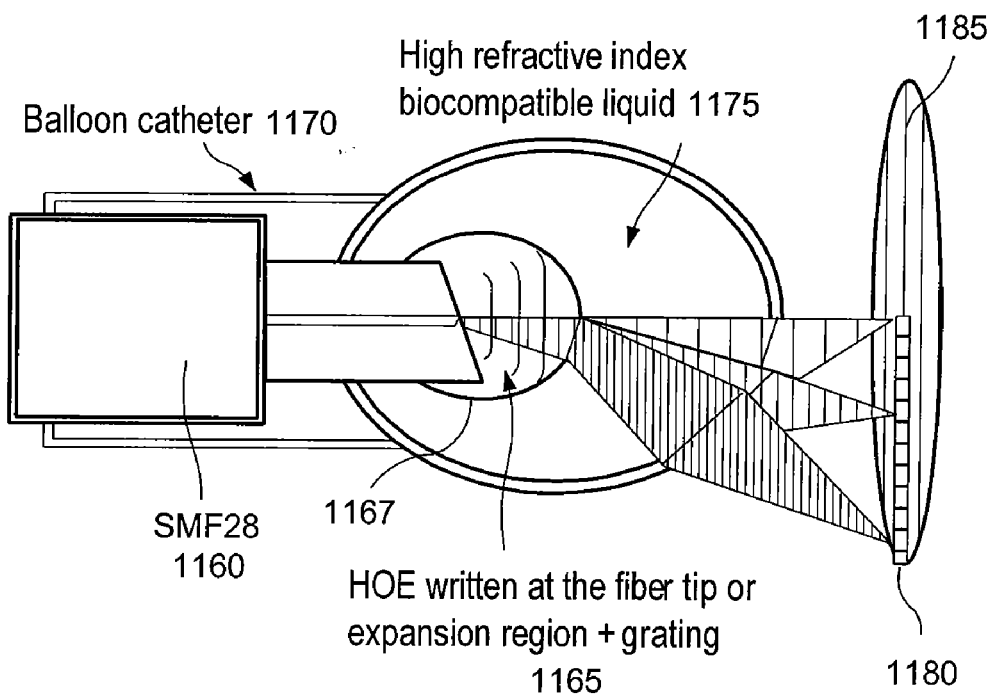
F I G. 11B

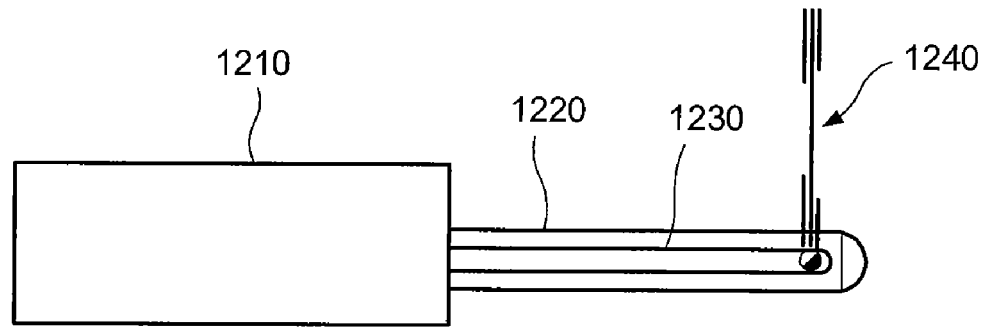
F I G. 12
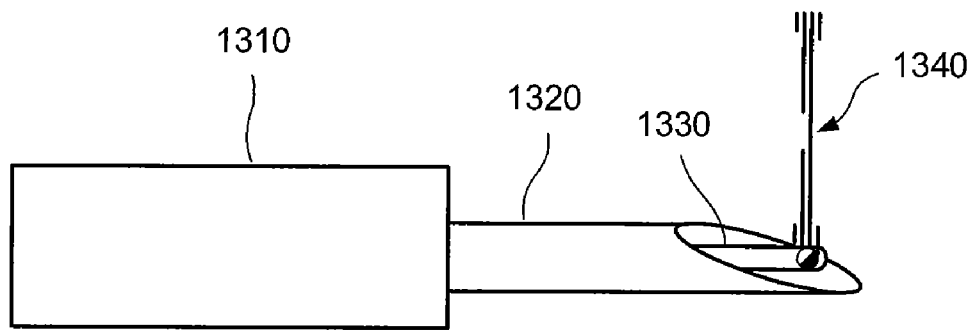
F I G. 13

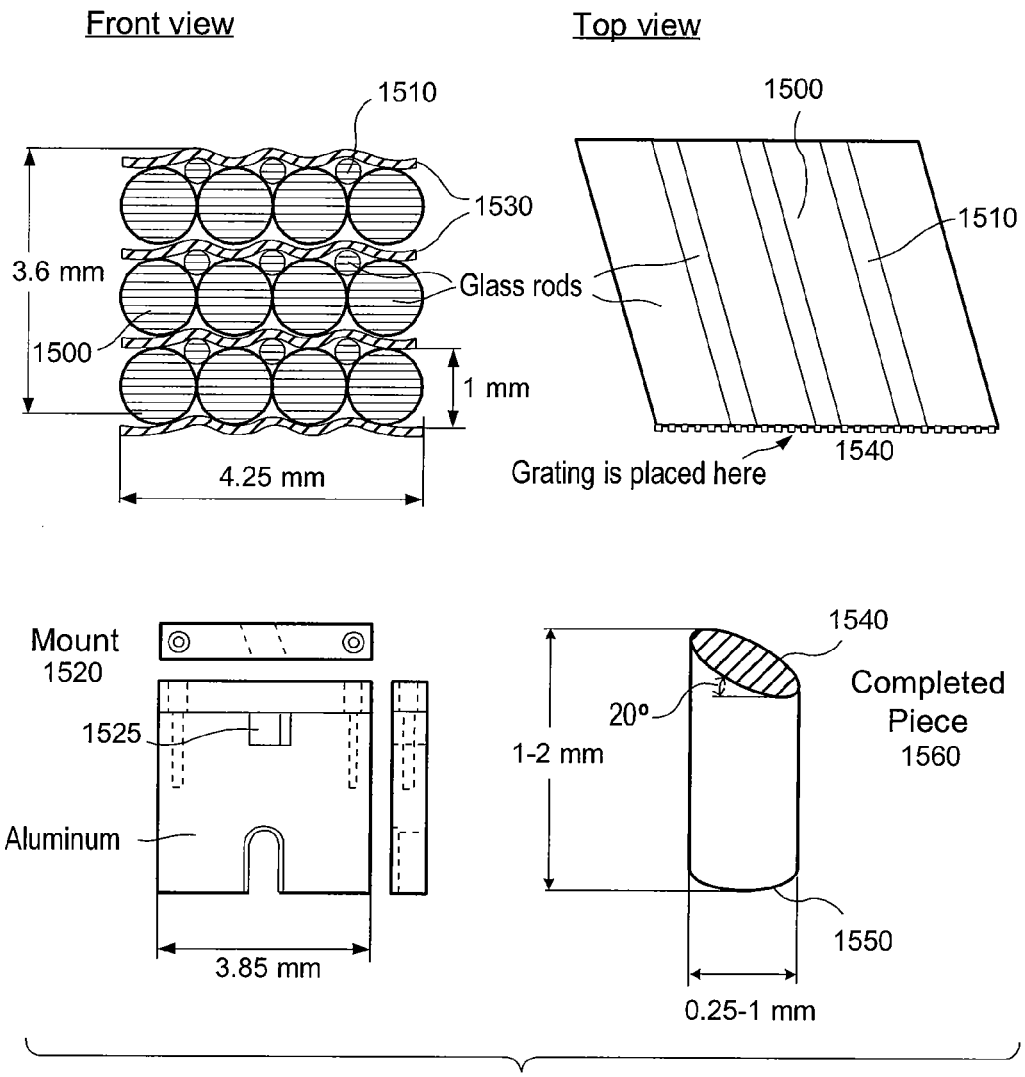
F I G. 15

APPARATUS FOR OBTAINING INFORMATION FOR A STRUCTURE USING SPECTRALLY-ENCODED ENDOSCOPY TECHNIQUES AND METHODS FOR PRODUCING ONE OR MORE OPTICAL ARRANGEMENTS

CROSS-REFERENCE TO RELATED APPLICATION(S)

This application is based upon and claims the benefit of priority from U.S. patent application Ser. No. 60/760,139, filed Jan. 19, 2006, the entire disclosure of which is incorporated herein by reference.

STATEMENT REGARDING FEDERALLY SPONSORED RESEARCH

The invention was made with the U.S. Government support under Contract No. BES-0086709 awarded by the National Science Foundation. Thus, the U.S. Government has certain rights in the invention.

FIELD OF THE INVENTION

The present invention relates generally to apparatus and method for spectrally encoded endoscopy and, more particularly to, e.g., apparatus for obtaining information for a structure using spectrally-encoded endoscopy techniques and method for producing one or more optical arrangements.

BACKGROUND OF THE INVENTION

Certain medical and technical applications utilize an ability to look inside the patient's body or use a particular device when the available pathways for probe advancement are of very narrow diameter (e.g., small vessels, small ducts, small needles, cracks etc.).

Conventional miniature endoscopes are generally composed of fiber-optic imaging bundles. These conventional instruments have diameters that range of from approximately 250 µm to 1.0 mm. Since optical fibers have a finite diameter, a limited number of fibers can be incorporated into one imaging bundle, resulting in a limited number of resolvable elements. The resultant image resolution and field of view provided by these imaging devices may be insufficient for obtaining endoscopic images of diagnostic quality in patients. The use of multiple fibers for imaging also increases the rigidity of the endoscopes, likely resulting in a bend radius of approximately 5 cm for the smallest probes in a clinical use. These technical limitations of fiber bundle microendoscopes, including a low number of resolvable points and increased rigidity, have limited the widespread use of miniature endoscopy in medicine.

U.S. Pat. No. 6,134,003 describes spectrally encoded endoscopy ("SEE") techniques and arrangements which facilitate the use of a single optical fiber to transmit one-dimensional (e.g., line) image by spectrally encoding one spatial axis. By mechanically scanning this image line in the direction perpendicular thereto, a two dimensional image of the scanned plane can be obtained outside of the probe. This conventional technology provides a possibility for designing the probes that are of slightly bigger diameter than an optical fiber. Probes in approximately 100 µm diameter range may be developed using such SEE technology.

SEE techniques and systems facilitate a simultaneous detection of most or all points along a one-dimensional line of the image. Encoding the spatial information on the sample can be accomplished by using a broad spectral bandwidth light source as the input to a single optical fiber endoscope.

FIG. 1 shows one such exemplary SEE system/probe 100. For example, at a distal end of the exemplary system/probe 100, light provided by the source can be transmitted via an optical fiber 110, and collimated by a collimating lens 120. Further, the source spectrum of the light can be dispersed by a dispersing element 130 (e.g., a diffracting grating), and focused by a lens 140 onto the sample. This optical configuration can provide an illumination of the sample with an array of focused spots 150 (e.g., on a wavelength-encoded axis), where each position (e.g., on the x-axis) can be encoded by a different wavelength (l). Following the transmission back through the optical fiber, the reflectance as a function of transverse location can be determined by measuring the reflected spectrum. High-speed spectral detection can occur externally to the probe and, as a result, the detection of one line of image data may not necessarily increase the diameter of the exemplary system/probe 100. The other dimension (e.g., y, slow scan axis) of the image can be obtained by mechanically scanning the optical fiber and distal optics at a slower rate.

Accordingly, it may be beneficial to address and/or overcome at least some of the deficiencies described herein above.

OBJECTS AND SUMMARY OF THE INVENTION

One of the objectives of the present invention is to overcome certain deficiencies and shortcomings of the prior art systems and methods (including those described herein above), and provide exemplary embodiments of systems and methods for generating data using one or more endoscopic microscopy techniques and, more particularly to e.g., generating such data using one or more high-resolution endoscopic microscopy techniques.

For example, certain exemplary embodiments of the present invention can facilitate the use and production of narrow diameter optical fiber probes that use exemplary SEE techniques. Certain procedures and configuration to achieve the preferable optical and mechanical functionality at the distal end of a narrow diameter fiber optical probe for SEE can be provided.

Different exemplary embodiments can be provided to incorporate the exemplary SEE optical functionality at a tip of the optical fiber in accordance with certain concepts of the present invention. For example, different types of fibers can be used depending on the spectral region and the size/flexibility preferences, e.g., single mode, multimode or double clad fibers can be used.

In one exemplary embodiment of the SEE system, the same channel can be used for illumination and collecting of the reflected light. Double clad fiber can be employed for improving the collecting efficiency and minimizing the speckle in the exemplary SEE system. For example, a regular telecommunication single mode fiber SMF28 can be used.

According to a particular exemplary embodiment of an apparatus for obtaining information for a structure according to the present invention can be provided. For example, the exemplary apparatus can include at least one first optical fiber arrangement which is configured to transceive at least one first electro-magnetic radiation, and can include at least one fiber. The exemplary apparatus can also include at least one second focusing arrangement in optical communication with the optical fiber arrangement. The second arrangement can be configured to focus and provide there through the first electromagnetic radiation. Further, the exemplary apparatus can include at least one third dispersive arrangement which is configured to receive a particular radiation which is the first electro-magnetic radiation and/or the focused electro-magnetic radiation, and forward a dispersed radiation thereof to at least one section of the structure. At least one end of the fiber can be directly connected to the second focusing arrangement and/or the third dispersive arrangement.

According to still another exemplary embodiment of the present invention, the end and/or the section can be directly connected to the third dispersive arrangement. The second focusing arrangement can include at least one optical element which may be directly connected to the end. The second arrangement may include an optical component with a numerical aperture of at most 0.2, and the optical element may be directly connected the optical component. The second arrangement may include an optical component with a numerical aperture of at most 0.2. The end may be directly connected to the optical component.

In yet another exemplary embodiment of the present invention, the particular radiation can include a plurality of wavelengths and/or a single wavelength that changes over time. The third dispersive arrangement may be configured to spatially separate the particular radiation into a plurality of signals having differing center wavelengths. The first, second and third arrangement can be provided in a monolithic configuration. The third dispersive arrangement may be a fiber grating, a blazed grating, a grism, a dual prism, a binary, prism and/or a holographic lens grating. The second focusing arrangement can include a gradient index lens, a reflective mirror lens grating combination and/or a diffractive lens.

According to a further exemplary embodiment of the present invention, at least one fourth arrangement can be provided which is configured to control a focal distance of the second focusing arrangement. The third dispersive arrangement may include a balloon. The second focusing arrangement and the third dispersive arrangement can be provided in a single arrangement. The single arrangement may be a holographic arrangement and/or a diffractive arrangement.

In addition, an exemplary embodiment of a method for producing an optical arrangement can be provided. For example, a first set of optical elements having a first size in a first configuration and a second set of optical elements in cooperation with the second set and having a second size in a second configuration can be provided. The first and second sets can be clamped into a third set of optical elements. The third set can be polished, and a further set of optical elements may be deposited on the polished set.

According to yet another exemplary embodiment of the present invention, the first set and/or the second set can be at least one set of cylindrical optical elements. At least one of the cylindrical optical elements may be an optical fiber. The third set may be polished at an angle with respect to the extension of at least one of the optical elements. The angle can substantially correspond to a Littrow's angle and/or be substantially greater than 1 degree. The further set may be a grating, and/or can include a diffractive optical element. A layer can be applied between elements of the first set and/or the second set. The layer may be composed of a thin material and/or a soft material.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 2 is a schematic diagram of an exemplary embodiment of an SEE imaging system/probe;

FIG. 3 is a schematic diagram of another exemplary embodiment of the SEE imaging system/probe, in which a prism is used as a dispersing element;

FIG. 4 is a schematic diagram of an additional exemplary embodiment of the SEE imaging system/probe, in which a micro spherical lens is used with the grating following a lens;

FIG. 5 is a schematic diagram of a further exemplary embodiment of the SEE imaging system/probe, which has a micro spherical lens design with the grating before the lens;

FIG. 9A is a schematic diagram of an exemplary embodiment of the endoscopic system/probe assembly having monolithic distal optics and a grism as a dispersing element in an exemplary configuration for side imaging;

FIG. 9B is a schematic diagram of another exemplary embodiment of the endoscopic system/probe assembly having monolithic distal optics and a double prism grism as a dispersing element in an exemplary configuration for forward imaging;

FIG. 10A is a schematic diagram of an exemplary embodiment of a cylindrical grating substrate with a tilted base for a Littrow regime;

FIG. 10B is a schematic diagram of an exemplary embodiment of a prismatic grating substrate with a tilted base for the Littrow regime;

FIG. 10C is a schematic diagram of another exemplary embodiment of the cylindrical grating substrate with a mirror tilted base and flatten side for the Littrow regime;

FIG. 10D is a schematic diagram another exemplary embodiment of the prismatic grating substrate with a mirror tilted base for the Littrow regime;

FIG. 11A is a schematic diagram of yet another exemplary embodiment of the endoscopic system/probe assembly in an exemplary balloon catheter configuration, in which approximately all of the optical functionality is transferred to the balloon by via HOE that is deposited on the balloon surface;

FIG. 11B is a schematic diagram of still another exemplary embodiment of the endoscopic system/probe assembly in balloon catheter configuration, in which at least some optical functionality is transferred to the balloon by the use of high refractive index transparent liquid to fill a thin wall balloon to form an inflatable focusing lens;

FIG. 12 is a schematic diagram of an exemplary embodiment of a catheter system/probe delivery technique using an exemplary guide catheter;

FIG. 13 is a schematic diagram of another exemplary embodiment of a catheter system/probe delivery procedure using an exemplary biopsy needle;

FIG. 15 is an illustration of procedural steps of an exemplary embodiment of a process for mounting grating substrates which can be facilitated for an exemplary grating fabrication process.

Figure 1:
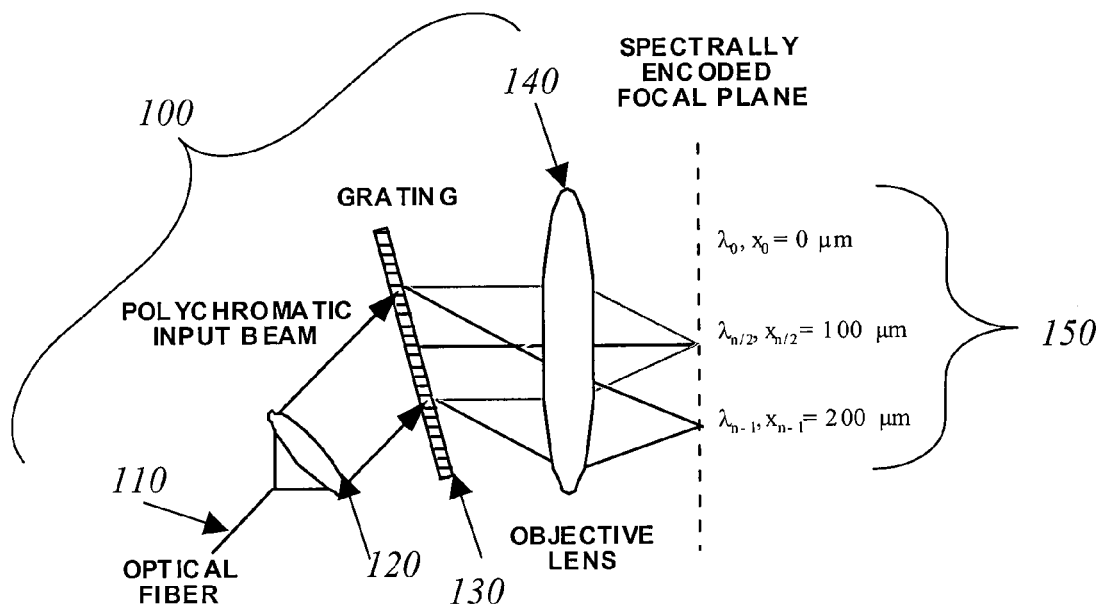
FIG. 1 is a schematic diagram of a procedure for implementing one-dimensional space-to-spectrum encoding.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

Prior to providing a detailed description of the various exemplary embodiments of the methods and systems for endoscopic microscopy according to the present invention, some introductory concepts and terminology are provided below. As used herein, the term "endoscopic probe" can be used to describe one or more portions of an exemplary embodiment of an endoscopic system, which can be inserted into a human or animal body in order to obtain an image of tissue within the body.

Prior to describing the exemplary embodiments of the systems and/or probes for spectrally encoded endoscopy according to the present invention, certain exemplary concepts and terminology are provided herein. For example, the term "endoscopic probe" may be used to describe a portion of an endoscopic system, which can be inserted into a human body in order to obtain an image of tissue within the human body. The term "monolithic" may be used to describe a structure formed as a single piece, which can have more than one optical function. The term "hybrid" may be used to describe a structure formed as a plurality of pieces, e.g., each piece having one optical function.

The exemplary embodiments of the system, apparatus, probe and method described herein can apply to any wavelength of light or electro-magnetic radiation, including but not limited to visible light and near infrared light.

FIG. 2 shows an exemplary embodiment of a SEE imaging system/probe 200 (e.g., endoscopic probe having a single mode fiber that deliver light from a light source to the tip of the fiber) which can include an optical fiber 210, an expansion region 220, a focusing region 230, an angled region 240 and a dispersing element 250 (e.g., grating). The exemplary system/probe 200 can generate a spectrally encoded imaging signal, e.g., a line 260 on the imaged surface with the longer wavelengths 280 deviated further from the probe axis than the shorter wavelengths 270.

The optical fiber 210 can be a single-mode fiber and/or a multi-mode fiber (e.g., preferably single mode for preserving the phase relation of the source light and the light remitted by the sample). By facilitation a light delivery through the optical fiber 210, SEE capabilities can be provided in a catheter or endoscope. Thus, a high-resolution microscopy of surfaces of the body accessible by endoscope can be facilitated by the exemplary embodiment of the system/probe 200.

A multiple of (e.g., four) distinct regions with specific optical properties can be used to determine the system/probe functionality.

For example, the expansion region can be used to facilitate the beam that is confined in the fiber core to expand and fill an aperture. The expansion region can be composed of optical glass (e.g., a piece of coreless fiber spliced to the main fiber and then cleaved to a predetermined length), optical epoxy, air, or transparent fluid. Index matching with the fiber core may be desirable for reducing the back reflection from the interface between the fiber and the expansion region. Other techniques and/or arrangements for reducing the back reflection, e.g., anti-reflection coating or angle cleaving, can be employed in case of air or other non-matching media used as an expansion region.

In the focusing region, the diverging beam can be transformed to a converging one. For example, a gradient index ("GRIN") lens or spherical micro lens can be used as shall be described in more detail below with reference to other exemplary embodiments. For example, the GRIN lens can be made by splicing a piece of GRIN fiber and cleaving it to a predetermined length. The spherical lens can be formed on the coreless fiber tip by melting it, by polishing, or by applying a small measured amount of optical epoxy.

The angled region can be used to support the dispersing element and/or provide an incidence tilt for the output direction and/or the desired regime (Litrow) in certain cases (e.g., a diffraction grating). As with the expansion region, different media can be used, and different techniques and/or arrangements for obtaining the desired tilt can be employed. For example, some of such exemplary techniques can include angle cleaving, polishing, molding of the optical epoxy etc.

The dispersing element can tilt different parts of the incident spectrum at different angles, thus producing the desired spatial spread of the incident light. It can be a prism made of high dispersion material or a high efficiency diffracting grating. It is possible to also produce a grating at the fiber tip. For example, transmitting or reflecting gratings can be used in different regimes depending on the application.

Figure 7:
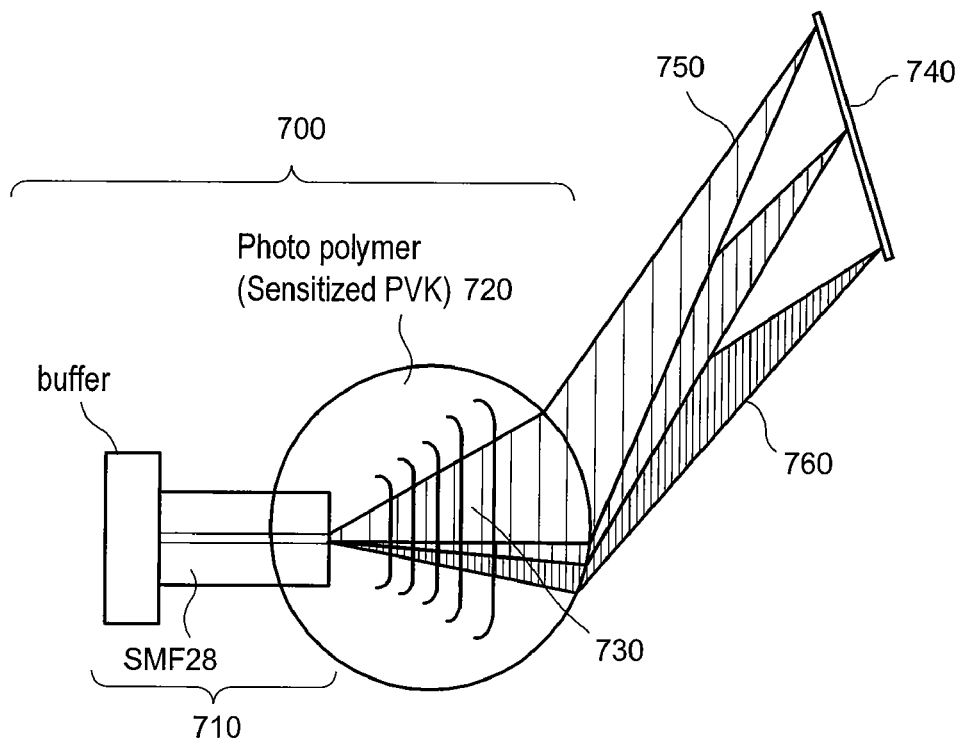
FIG. 7 is a schematic diagram of an exemplary embodiment of an endoscopic system/probe that can use a holographic optical element ("HOE") formed in a drop of photo-sensitized polymer combining the functionality of expansion, focusing and dispersing regions.

Other numerous combinations and permutations of the above-mentioned regions can provide a functional system/probe, certain exemplary embodiments of which shall be described in further detail below. For example, two general types of dispersing elements can be used: prism or diffracting grating. The holographic optical element that combines the dispersing power of the grating and the focusing power of a lens can also be used as shown in FIG. 7.

Prism made of dispersing material can be used when the light source has a very broad spectrum, e.g., a femto-second laser source with microstructured fiber for super-continuum generation. In such exemplary source, the spectrum can span in visible and near infrared.

FIG. 3 shows another exemplary embodiment of the SEE system/probe 300 which can include a single mode optical fiber 310 spliced to a coreless fiber 320 (e.g., the expansion region). Further, a short piece of gradient refracting index (GRIN) fiber 330 can be spliced to the coreless fiber (e.g., the focusing region). In addition, another short piece of coreless fiber 340 can be spliced to the focusing region 330. The output surface 350 may be angle polished/cleaved, thus forming a refracting boundary between the fiber 340 and the external medium 355 (e.g., air, water or other liquid). In FIG. 3, an exemplary use of the prism 340 is illustrated as a dispersive element. With an anti-reflecting coating on the output surface 350, this exemplary configuration can provide a high transmission efficiency. It may be desirable for the angled region to be made of a highly dispersive material. In the case of a normal dispersion, longer wavelength parts of the original spectrum 370 may deviate less than the shorter wavelengths 380, thus forming the imaging line 360.

Diffracting gratings can be preferable in the case of narrow band source because of the higher dispersing power that can be achieved with such gratings. For example, the transmission and reflection diffracting gratings can be used. FIG. 5 shows a schematic diagram of a further exemplary embodiment of the SEE imaging system/probe 500, which has a micro spherical lens 530 with a grating 550 provided before the lens 530 use of the reflection diffracting grating. In other exemplary configuration, the use of reflection diffracting grating utilizes a housing that can enlarge the system/probe. The additional details of the exemplary embodiment of the SEE system/probe 500 shall be described in further detail below.

The selected dispersing element can be a transmission diffracting grating. It is also possible to use other grating, e.g., a volume holographic grating or a surface phase grating. The volume holographic gratings can exhibit a higher efficiency, but are less common, and some of the materials used therefore generally require sealing from the humidity, as well as more expensive and difficult to replicate. The surface phase gratings may be less efficient, but are easy to replicate and mass-produce when a master grating is made. For both of these exemplary elements, the grating can be a thin film (~5-10 μm) that is applied to the angled region.

FIG. 4 shows another exemplary embodiment of the SEE system/probe 400 which can include a single mode optical fiber 410 spliced to a coreless fiber 420. In this exemplary embodiment, the tip of the expansion region 420 can be melted to form a small spherical surface 425, and then a low refractive index epoxy 430 may be used to attach the grating 440 at an angle to the system/probe 400. In this exemplary system/probe 400, the focusing region can be the surface that separates the expansion region and the angled region. The longer wavelengths 460 of the original spectrum may deviate more than the shorter wavelengths 470, thus possibly forming the imaging line 450.

FIG. 5 shows the exemplary SEE probe 500 described above, which can include a single mode optical fiber 510 spliced to a coreless fiber 520. The tip of the expansion region 520 can be melted to form a ball 530. The ball may be polished at an angle (Littrow) and on the flat surface 540 that can result from this exemplary procedure, a reflecting grating 550 may be deposited. The light beam can expand in the expansion section after exiting an end 510 of the core of the optical fiber 510, and may then be dispersed by the grating 550. Different monochromatic beams that can result may then be focused by the near spherical surface of the glass ball to form the imaging line 560. The dispersing element may be provided before the focusing element. The longer wavelengths 580 of the original spectrum may deviate more than the shorter wavelengths 570.

Figure 6:
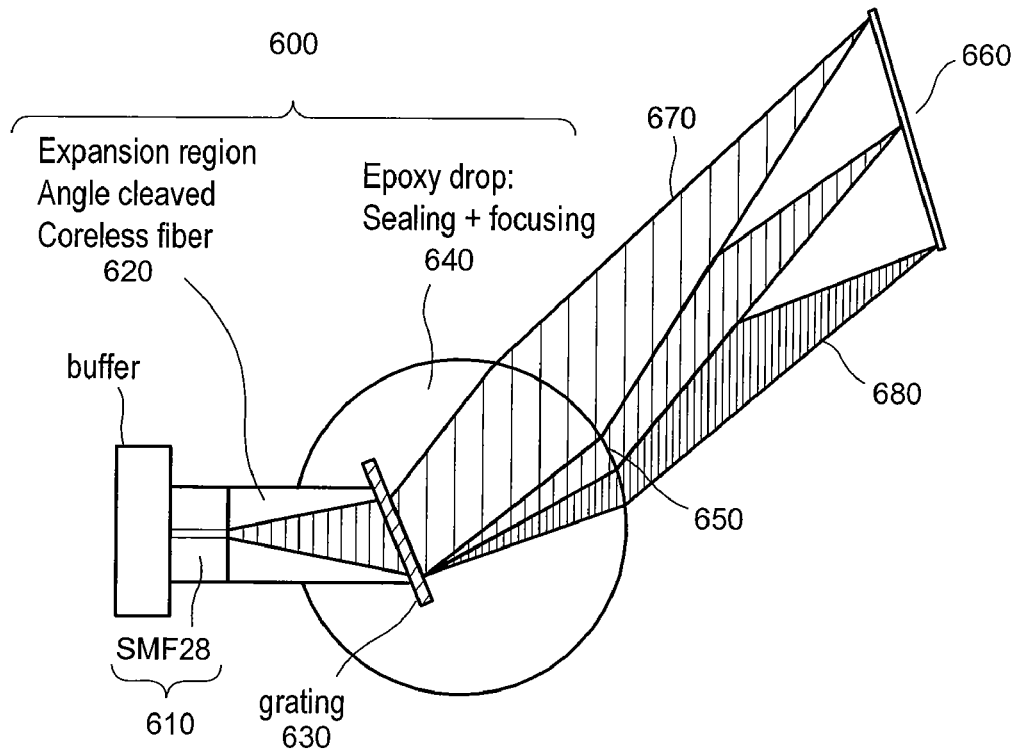
FIG. 6 is a schematic diagram of an exemplary embodiment of a micro spherical lens configuration with the grating provided before the lens, and in which the lens can be formed by a drop of optical epoxy at a tip of a fiber.

FIG. 6 shows another exemplary embodiment of the SEE system/probe 600 which may include a single mode optical fiber 610 spliced to a short piece of coreless fiber 620 that may be angle cleaved or polished at an angle (which can be the Littrow angle for the grating 630) and the grating 630 may be deposited on the tip of the expansion region 620. A drop of an optical epoxy 640 can be cured at the tip of the fiber 610 to protect the transmission grating 630 and form the focusing surface 650. The dispersing element 630 can be provided before the focusing element 650, and the expansion region 620 and the angled region 620 may coincide. The longer wavelengths 670 of the original spectrum may deviate more than the shorter wavelengths 680 to form the imaging line 660.

FIG. 7 shows yet another exemplary embodiment of the SEE system/probe 700, which can include a single mode optical fiber 710. A holographic optical element ("HOE") 730 written in a drop of photosensitive polymer 720 can incorporate the optical functionality of the expansion, focusing and dispersing elements. The longer wavelengths 750 of the original spectrum can deviate more than the shorter wavelengths 760 to form the imaging line 740.

Figure 8:
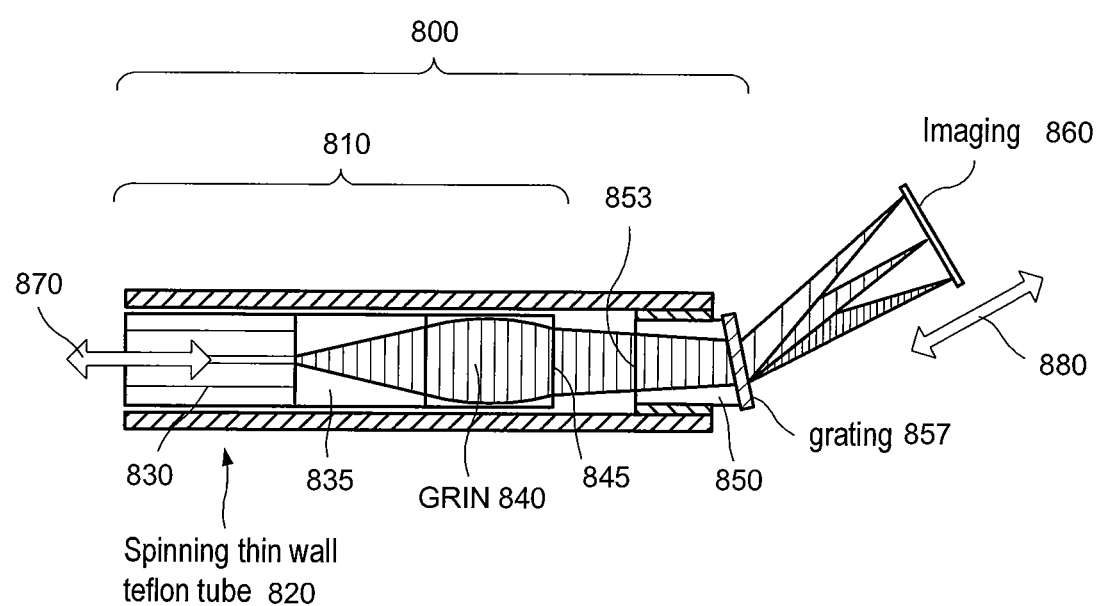
FIG. 8 is a schematic diagram of an exemplary embodiment of the endoscopic system/probe assembly that may be non-monolithic to facilitate zooming and/or refocusing.

FIG. 8 shows still another exemplary embodiment of the SEE system/probe 800 that can provide radiation 870 there through, and which can include a static monolithic core 810 and a spinning flexible thin wall Teflon tubing 820 with the angled region 850 attached to its end. An optical fiber 830, an expansion region 835, and a focusing region 840 may be attached/glued/spliced together to form the core 810. A dispersing element/grating 857 can be deposited on the tilted output surface of the angled region 850. The glass-to-air interfaces of the focusing region 840 845 and the angled region 850 853 may be anti-reflection coated. Changing the gap between such elements by advancing the core 810 can effectively change the distance 880 of the imaging line 860 to the output surface of the system/probe 800 (e.g., the grating 875).

Exemplary non-monolithic configurations similar to those shown in the exemplary embodiment of FIG. 8 can allow for additional functionality such as zooming and/or focusing to be provided in the distal probe end. Multi-lens configurations may also be implemented.

The use of a prism-grating combination (grism) may facilitate a control of the angle of incidence and the probe output direction. Exemplary arrangement which implements such configurations are shown in FIG. 9A and FIG. 9B. In particular, FIG. 9A shows a further exemplary embodiment of the SEE imaging system/probe 900 which can include a static sheath 905 with a transparent window 908 and a monolithic optical core 910 that can be scanned. The core can include an optical fiber 915, an expansion region 917, a focusing element (e.g., a GRIN lens) 920, and a prism 925 with the grating 930 deposited on its output surface. The optical elements may be maintained together with a micro mechanical housing 940. This exemplary configuration may represent a side looking imaging system/probe.

FIG. 9B shows still another exemplary embodiment of the SEE imaging system/probe 950 which can include a static sheath 955 with a transparent window 958 and a monolithic optical core 960 that can be scanned. The core can include an optical fiber 965, an expansion region 967, and a focusing element (GRIN lens) 970. A grating 980 may be sandwiched between prisms 975 and 977. The optical elements may be maintained together with a micro mechanical housing 990. This exemplary configuration can represent a forward-looking imaging system/probe.

It may be beneficial for this exemplary application to utilize a grating in Littrow regime when the angle of incidence is equal to the angle of diffraction (e.g., for the central wavelength). In this exemplary configuration, the shape of the beam may not change after the grating, and thus provide an effective regime. FIGS. 10A-10C illustrate exemplary embodiments of the substrate that can provide a Littrow regime for the grating.

For example, FIG. 10A shows an exemplary embodiment of a diffracting grating substrate 1000 which can include a cylindrical body 1005 with one side 1020 polished at the Littrow's angle 1015. FIG. 10B shows another exemplary embodiment of the diffracting grating substrate 1025 which includes a prismatic body 1030 with one side 1045 polished at the Littrow's angle 1040. FIG. 10C shows still another exemplary embodiment of the diffracting grating substrate 1050 which can include a cylindrical body 1055 with one side 1057 polished at the complimentary to Littrow's angle 1058 and a mirror 1059 deposited. Another flat surface 1065 may be polished parallel to the cylinder axis where the grating is to be deposited. FIG. 10D shows yet another exemplary embodiment of the diffracting grating substrate 1075 with a flat surface 1167 which can include a prismatic body 1080 with one side 1087 polished at the complimentary to Littrow's angle 1085 and a mirror 1087 deposited. The grating is intended to be deposited on the side 1095. It should be understood that the illustrated sizes are merely exemplary, and other sizes are possible and are within the scope of the present disclosure.

In certain exemplary applications, the system/probe can be small enough to be introduced through a small opening, and big enough to be able to image at big distances in a cavity. These conflicting preferences can be met by using an inflating balloon with added optical functionality. Two such exemplary configurations are shown in FIGS. 11A and 11B.

In particular, FIG. 11A shows another exemplary embodiment of the SEE system/probe 1100 which can include a single mode optical fiber 1110. A holographic optical element ("HOE") 1125 written on the surface of the inflating balloon 1120 can incorporate the optical functionality of the focusing and dispersing elements. The dispersed light may be focused into the imaging line 1130. When the exemplary system/probe 1100 is spun, the image of the area 1135 may be obtained. This exemplary configuration may be further defined by the material availability for infrared applications and the possible difficulties associated with the holographic process.

FIG. 11B shows still another exemplary embodiment of the SEE system/probe 1150 which can include a single mode optical fiber 1160. A holographic optical element ("HOE") 1165 written in a drop of photosensitive polymer 1067 deposited on the tip of the fiber 1060 can incorporate the optical functionality of the expansion, and dispersing elements. Further, the balloon catheter 1170 may be filled with a high refractive index biocompatible liquid, thus forming a near spherical refracting focusing surface 1175. This exemplary configuration may be further defined by the material availability for infrared applications and the possible difficulties associated with the holographic process.

One exemplary advantage of the various exemplary embodiments of the present invention may be the relative simple configurations and designs of the exemplary embodiments of the systems/probes. According to one exemplary embodiment, e.g., the system/probe can include an optical fiber with a modified tip. (See FIGS. 2-7). For example, the system/probe can illuminate a line at the object and acquire one line of image at a time. In order to acquire an image with this exemplary system/probe, it may be preferable that the imaging line is scanned in transverse direction across the object. This can be a repetitive or a single scan. In such cases, an image or the surface that the line scans can be acquired and displayed. The information obtained from the back-scattered light can be interpreted in various manners to represent different tissue types, different states of the same tissue, various types of dysphasia, tissue damage etc. as well as motion of body liquids and cells. Certain exemplary arrangements which can be used for placing the probe and scanning the tissue may be as follows.

Catheter Exemplary Embodiments

Where catheters are used in medicine, a very thin wall sealed PTFE tube can be used as a protective transparent sheath for the probe that can be delivered through the lumen of a guide catheter to the area of interest (as shown in FIG. 12). When in place, the fiber inside the thin tube can be scanned by rotating or by pulling in order to obtain an image. A short distal part of the catheter can be of a small diameter. The proximal end can be of a bigger diameter with added additional springs/shafts to protect the fiber and convey the motion.

For example, FIG. 12 shows an exemplary embodiment of a catheter of the SEE system/probe 1200 which can include an optical core 1230. The exemplary system/probe 1200 can be protected by a transparent sheath 1220 that can allow the transmission of the imaging light 1240 into the region of interest. The imaging catheter 1220 can be placed trough a guide catheter 1210.

Needle Exemplary Embodiments

For needle biopsies that are traditionally performed under CT, MRI, or ultrasound guidance, the fiber optic probe may be inserted into the biopsy needle (as shown in FIG. 13). In this exemplary configuration, the fiber optic probe may be embedded within the needle biopsy device or inserted through the lumen of the needle. The image can be acquired during the insertion of the needle or by rotating of the probe inside the needle and, e.g., only looking at a limited angle FIG. 13 shows another exemplary embodiment of a catheter of the SEE system/probe 1300 which can include an optical core 1330 which facilitates the transmission of the imaging light 1340 into the region of interest. The exemplary system/probe 1300 can be delivered to the region being imaged through the lumen of a biopsy needle 1320 that may be delivered through an endoscope or guide catheter 1310.

Intraoperative Exemplary Embodiments

For example, the exemplary system/probe may be incorporated into an electrocautery device, scalpel, or be an independent hand-held device.

Exemplary Optical Parameters

One exemplary parameter for comparing different miniature endoscope technologies may be the number of resolvable points. This exemplary parameter can be the limiting factor that may render a technology more or less useful for the particular application. The total number of resolvable points provided by the exemplary embodiments of the SEE system/probe (n) for the first diffraction order can be defined by:

$$n = \left(\frac{\Delta \lambda d}{\lambda_0 \Lambda \cos(\theta_i)}\right)^2$$

Exemplary determinations can indicate that for a source with a center wavelength, $\lambda_0$, source bandwidth, $\Delta\lambda$, of 250 nm, a grating input angle, $\theta_i$, of 49° and a grating groove density, $\Lambda$, of 1800 lines per mm, a 250 μm diameter SEE probe may facilitate imaging with, e.g., 40,000 resolvable points. In comparison, a commercially available 300 μm diameter fiber-optic image bundle (Holl Meditronics, 30-0084-00) contains only 1,600 resolvable points.

Figure 14:
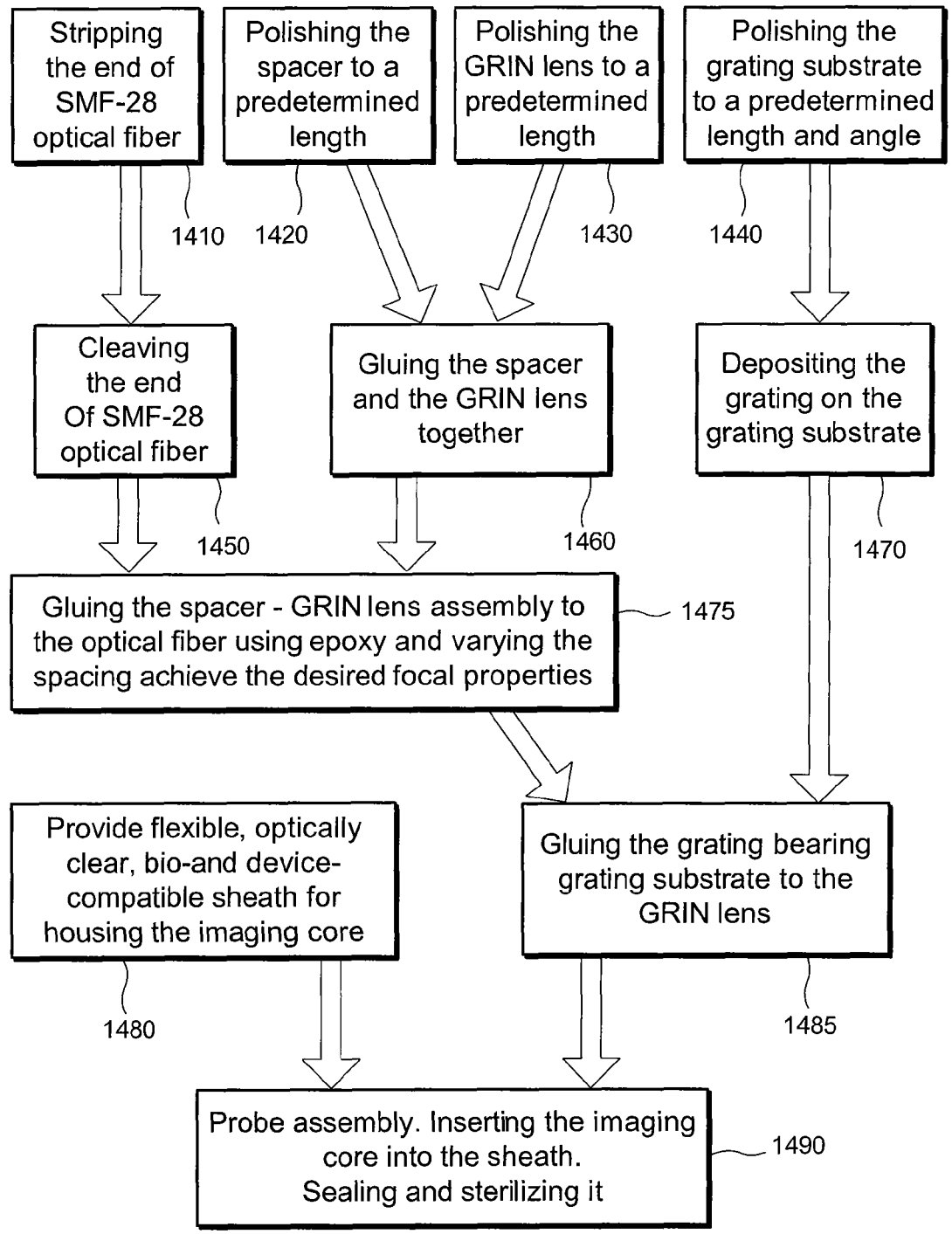
FIG. 14 is a flow diagram of a method according to an exemplary embodiment of the present invention for making the exemplary embodiment of the SEE system/probe shown in FIG. 2.

FIG. 14 shows a flow diagram of a method according to an exemplary embodiment of the present invention for making the exemplary embodiment of the SEE system/probe shown in FIG. 2. In particular, the end of SMF-28 optical fiber 210 or any other optical fiber can be stripped (step 1410). In step 1420, the spacer can be polished to a predetermined length. The GRIN lens can be polished to a predetermined length in step 1430. Further, in step 1440, the grating 250 can be polished to a predetermined length and angle.

The results of step 1410 are provided to step 1450, in which the end of the optical fiber is cleaved. The results of steps 1420 and 1430 are provided to step 1460, in which the spacer and GRIN lens are glued together. The results of step 1440 are provided to step 1470, in which the grating 250 is deposited on the grating substrate. The results of steps 1450 and 1460 are provided to step 1475, in which the spacer-GRIN lens assembly is glued to the optical fiber using an optical epoxy and the spacing is varied to achieve the desired focal properties. The results of steps 1475 and 1470 are provided to step 1485 in which the grating 250 bearing the grating substrate is glued to the GRIN lens. In step 1480, flexible, optically clear, bio- and device-compatible sheath can be provided for housing the imaging core. The results of steps 1480 and 1485 are forwarded to step 1490, in which the exemplary system/probe is assembled, e.g., by inserting the core into the sheath and sealing and sterilizing the resultant assembly.

FIG. 15 shows an illustration of procedural steps of an exemplary embodiment of a process for mounting grating substrates which can be facilitated for an exemplary grating fabrication process. It should be understood that dimensions provided in FIG. 15 are exemplary, and numerous other dimensions can be utilized in accordance with the exemplary embodiments of the present invention. For example, several glass rods with different diameters 1500, 1510 can be stacked and mounted together inside a particular mount 1520 into a particular location 1525. The rods can be separated by a thin lead foil 1530 (e.g., 127 mm thick). The rod stack can then be polished at an angle while inside the mount 1520. After polishing, the polished face can be cleaned, and a grating 1540 may be fabricated, e.g., without disassembling the pieces. When grating fabrication is completed, the pieces can be disassembled. The individual pieces may then be polished from the other side 1550. The completed grating 1560 can then be assembled into the fiber or lens.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with and/or implement any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus obtaining information for a structure, comprising:
    at least one first optical fiber arrangement configured to transceive at least one first electro-magnetic radiation, and including at least one fiber;
    at least one focusing second arrangement in optical communication with the at least one first optical fiber arrangement, the at least one second arrangement being configured to focus and provide there through the at least one first electro-magnetic radiation to generate a focused electro-magnetic radiation; and
    at least one dispersive third arrangement including a balloon, and configured to (i) receive a particular radiation which is at least one of the at least one first electro-magnetic radiation or the focused electro-magnetic radiation, and (ii) forward a dispersed radiation thereof to at least one section of the structure,
    wherein at least one end of the at least one fiber is directly connected to at least one of the at least one focusing second arrangement or the at least one dispersive third arrangement.

2. The apparatus according to claim 1, wherein the at least one end is directly connected to the at least one dispersive arrangement.

3. The apparatus according to claim 1, wherein the at least one section is directly connected to the at least one dispersive arrangement.

4. The apparatus according to claim 1, wherein the at least one focusing arrangement comprises at least one optical element which is directly connected to the at least one end.

5. The apparatus according to claim 4, wherein the at least one focusing arrangement includes an optical component with a numerical aperture of at most 0.2, and wherein the at least one optical element is directly connected to the optical component.

6. The apparatus according to claim 1, wherein the at least one focusing arrangement includes an optical component with a numerical aperture of at most 0.2.

7. The apparatus according to claim 6, wherein the at least one end is directly connected to the optical component.

8. The apparatus according to claim 1, wherein the particular radiation comprises at least one of a plurality of wavelengths or a single wavelength that changes over time.

9. The apparatus according to claim 1, wherein the at least one dispersive arrangement is configured to spatially separate the particular radiation into a plurality of signals having differing center wavelengths.

10. The apparatus according to claim 1, wherein the first, second and third arrangements are provided in a monolithic configuration.

11. The apparatus according to claim 1, wherein the at least one dispersive arrangement is at least one of a fiber grating, a blazed grating, a grism, a dual prism, a binary prism or a holographic lens grating.

12. The apparatus according to claim 1, wherein the at least one focusing arrangement contains at least one of a gradient index lens, a reflective mirror lens grating combination or a diffractive lens.

13. The apparatus according to claim 1, further comprising at least one fourth arrangement which is configured to control a focal distance of the at least one focusing arrangement.

14. The apparatus according to claim 1, wherein the at least one focusing arrangement and the at least one dispersive arrangement are provided in an enclosure.

15. The apparatus according to claim 14, wherein the enclosure is part of at least one of a holographic arrangement or a diffractive arrangement.

16. The apparatus according to claim 1, wherein the at least one structure is an anatomical structure, and the at least one dispersive arrangement forwards the dispersed radiation to the anatomical structure.

\* \* \* \* \*